United States Patent [19]
Eide et al.

[11] Patent Number: 5,962,500
[45] Date of Patent: Oct. 5, 1999

[54] INSULIN SENSITIVITY WITH ANGIOTENSIN II RECEPTOR BLOCKING IMIDAZOLES

[76] Inventors: Ivar K. Eide; Andreas Moan; Sverre E. Kjeldsen, all of P.O. Box 2000, Rahway, N.J. 07065

[21] Appl. No.: 09/128,138

[22] Filed: Aug. 3, 1998

Related U.S. Application Data

[63] Continuation of application No. 08/958,236, Oct. 27, 1997, abandoned, which is a continuation of application No. 08/775,696, Dec. 31, 1996, abandoned, which is a continuation of application No. 08/406,620, Mar. 20, 1995, abandoned.

[30] Foreign Application Priority Data

Mar. 31, 1994 [GB] United Kingdom .................. 9406573

[51] Int. Cl.$^6$ .................................................. A01N 43/38
[52] U.S. Cl. .......................... 514/410; 514/359; 514/385; 514/396; 514/397
[58] Field of Search .................................. 514/410, 385, 514/396, 397, 359

[56] References Cited

U.S. PATENT DOCUMENTS

| | | |
|---|---|---|
| 5,138,069 | 8/1992 | Carini et al. . |
| 5,264,447 | 11/1993 | Ohtawa . |
| 5,266,583 | 11/1993 | Ohtawa . |

OTHER PUBLICATIONS

A. Moan et al.; "Agiotensin II (AII) Receptor Antagonism with Losartan Increases Insulin Sensitivity and Decreases Sympathetic Nervous System Activity in Essential Hypertension"Inter. Soc. Hypertension, (1994).

A. Moan, et al., "The Effect Of Angiotensin II Receptor Blockade On Insulin Sensitivity And Sympathetic Nervous System Activity In Primary Hypertension", Blood Pressure, vol. 3 pp. 185–188, (1994).

A. Moan,et al., "Hypertension Therapy And Risk Of Coronary Heart Disease: How Do Antihypertensivies Affect Metabolic Factors?", Cardiology, vol. 86, pp. 89–93 (1995).

A. Moan, et al., "Angiotension II (A–II) Receptor Antagonism With Losartan Increases Insulin Sensitivity And Decreases Sympathetic Nervous System (SNS) Activity In Essential Hypertension", Int'l. Soc. Of Hypertension, pp. 21–25 (1994).

O. Iimura, et al., STN International File Biosis., STN ACC. No. 94:417516 Nineth Scientific Meeting of the Am. Society Hypertension, May 11–14, (1994), Am. J. of Hypertension 7 (4 part 2), (1994).

H. Tomiyama, et al., "Kinins Contribute to the Improvement of Insulin Sensitivity During Treatment With Angiotensin Converting Enzyme Inhibitor", Hypertension, vol. 23(4), pp. 450–455, (1994).

G. Bonner, "Hemmung des Renin–Angiotensin–Systems als Antihypertensives Prinzip", Munch. Med. Wschr., vol. 136(47), pp. 727–730, (1994).

K. Shimamoto, et al., "Effects of an Angiotensin II Receptor Antagonist, TCV–116, on Insulin Sensitivity in Fructose–Fed Rats", Blood Pressure, vol. 3(5), pp. 113–116, (1994).

H. Tomiyama, et al., "Role of Kinins in Different Responses of Insulin Sensitivity by Converting Enzyme Inhibitor, Angiotensin II Antagonist and Alpha 1–Blocker", Hypertension, vol. 20(3), p. 411, (1992).

*Primary Examiner*—John M. Cooney, Jr.
*Attorney, Agent, or Firm*—Valerie J. Camara; Mark R. Daniel

[57] ABSTRACT

This invention relates to a novel method of using an Angiotensin II antagonist for the improvement of insulin sensitivity alone or in conjunction with the treatment of hypertension. Angiotensin II antagonists such as the class of substituted imidazoles represented by formula I:

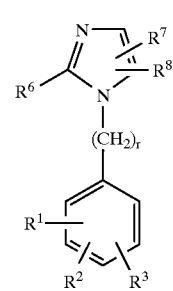

and specifically by Losartan, 2-butyl-4-chloro-1-[(2'-tetrazol-5-yl)biphenyl-4-yl]methyl]-5-(hydroxymethyl) imidazole potassium salt.

7 Claims, No Drawings

INSULIN SENSITIVITY WITH ANGIOTENSIN II RECEPTOR BLOCKING IMIDAZOLES

This is a of application Ser. No. 08/958,236 filed Oct. 27, 1997, now abandoned; which is a continuation of application Ser. No. 08/775,696 filed Dec. 31, 1996, now abandoned; which is a continuation of application Ser. No. 08/406,620 filed Mar. 20, 1995, now abandoned.

FIELD OF THE INVENTION

This invention relates to a novel method of using an angiotensin II receptor antagonist, such as substituted imidazole compounds, for the improvement of insulin sensitivity alone or in conjunction with the treatment of hypertension. The invention also relates to a method of using an angiotensin II receptor antagonist, such as substituted imidazoles in conjunction with a diuretic for the improvement of insulin sensitivity.

Substituted imidazoles of formula I are known to inhibit the action of the octapeptide hormone angiotensin II (AII) and are useful therefore in alleviating angiotensin induced hypertension. The enzyme renin acts on a blood plasma $\alpha_2$-globulin, angiotensinogen, to produce angiotensin I, which is then converted by angiotensin converting-enzyme to AII. The latter substance is a powerful vasopressor agent which has been implicated as a causitive agent for producing high blood pressure in various mammalian species, such as the rat, dog, and man. The compounds disclosed in this application inhibit the action of AII at its receptors on target cells and thus prevent the increase in blood pressure produced by this hormone-receptor interaction. The instant application discloses a method for the improvement of insulin sensitivity by administering an angiotensin II receptor antagonist, such as a substituted imidazole of formula I, to a species of mammal with hypertension due to angiotensin II. Administration of an angiotensin II receptor antagonist, such as a substituted imidazole of formula I, with a diuretic, such as furosemide or hydrochlorothiazide, either as a stepwise combined therapy (diuretic first) or as a physical mixture, enhances the antihypertensive effect of the compound, while also improving the insulin sensititvity of the patient.

K. Matsumura, et al., in U.S. Pat. No. 4,207,324 issued Jun. 10, 1980, discloses 1,2-disubstituted-4-haloimidazole-5-acetic acid derivatives of the formula:

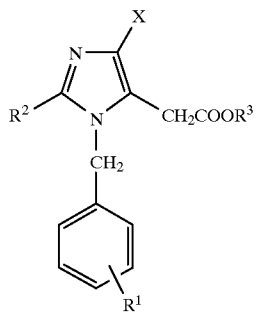

Wherein $R^1$ is hydrogen, nitro or amino; $R^2$ is phenyl, furyl or thienyl optionally substituted by halogen, lower alkyl, lower alkoxy or di-lower alkylamino; $R^3$ is hydrogen or lower alkyl and X is halogen; and their physiologically acceptable salts. These compounds have diuretic and hypotensive actions.

Furukawa, et al., in U.S. Pat. No. 4,355,040 issued Oct. 19, 1982, discloses hypotensive imidazole-5-acetic acid derivatives having the formula:

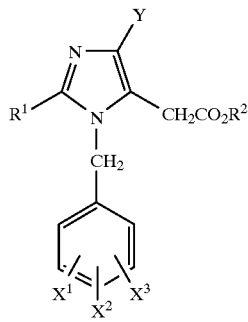

Wherein $R^1$ is lower alkyl, cycloalkyl, or phenyl optionally substituted; $X^1$, $X^2$, and $X^3$ are each hydrogen, halogen, nitro, amino, lower alkyl, lower alkoxy, benzyloxy, or hydroxy; Y is halogen and $R^2$ is hydrogen or lower alkyl; and salts thereof.

Furukawa, et al., in U.S. Pat, 4,340,598, issued Jul. 20, 1982, discloses hypotensive imidazole derivatives of the formula:

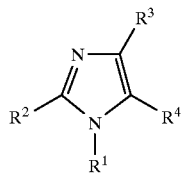

Wherein $R^1$ is lower alkyl or, phenyl $C_{1-2}$ alkyl optionally substituted with halogen or nitro; $R^2$ is lower alkyl, cycloalkyl or phenyl optionally substituted; one of $R^3$ and $R^4$ is $—(CH_2)_n COR^5$ where $R^5$ is amino, lower alkoxyl or hydroxyl and n is 0, 1, 2 and the other of $R^3$ and $R^4$ is hydrogen or halogen; provided that $R^1$ is lower alkyl or phenethyl when $R^3$ is hydrogen, n=1 and $R^5$ is lower alkoxyl or hydroxyl; and salts thereof.

Furukawa, et al., in European Patent Application 103,647 discloses 4-chloro-2-phenylimidazole-5-acetic acid derivatives useful for treating edema and hypertension of the formula:

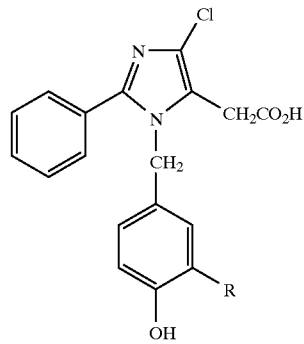

Where R represents lower alkyl and salts thereof.

The metabolism and disposition of hypotensive agent 4-chloro-1-(4-methoxy-3-methylbenzyl)-2-phenyl-imidazole-5-acetic acid is disclosed by H. Torii in *Takeda Kenkyushoho*, 41, No 3/4, 180–191 (1982).

Frazee, et al., in European Patent Application 125,033-A discloses 1-phenyl(alkyl)-2-(alkyl)-thioimidazole derivatives which are inhibitors of dopamine-β-hydroxylase and are useful as antihypertensives, diuretics and cardiotonics.

European Patent Application 146,228 filed Oct. 16, 1984, by S. S. L. Parhi discloses a process for the preparation of 1-substituted-5-hydroxymethyl-2-mercaptoimidazoles.

A number of references disclose 1-benzyl-imidazoles such as U.S. Pat. Nos. 4,448,781 to Cross and Dickinson (issued May 15, 1984); 4,226,878 to Ilzuka, et al. (issued Oct. 7, 1980); 3,772,315 to Regel, et al. (issued Nov. 13, 1973); 4,379,927 to Vorbruggen, et al. (issued Apr. 12, 1983); amongst others.

Pals, et al., *Circulation Research*, 29, 673 (1971) describe the introduction of a sarcosine residue in position 1 and alanine in position 8 of the endogenous vasoconstrictor hormone AII to yield an (octa)peptide that blocks the effects of AII on the blood pressure of pithed rats. This analog, [$Sar^1$, $Ala^8$] AII, initially called "P-113" and subsequently "Saralasin," was found to be one of the most potent competitive antagonists of the actions of AII, although, like most of the so-called peptide-AII-antagonists, it also possesses agonistic actions of its own. Saralasin has been demonstrated to lower arterial pressure in mammals and man when the (elevated) pressure is dependent on circulating AII (Pals et al., *Circulation Research*, 29, 673 (1971); Streeten and Anderson, Handbook of Hypertension, Vol. 5, Clinical Pharmacology of Antihypertensive Drugs, A. E. Doyle (Editor), Elsevier Science Publishers B. V., p. 246 (1984)). However, due to its agonistic character, saralasin generally elicits pressor effects when the pressure is not sustained by AII. Being a peptide, the pharmacological effects to saralasin are relatively short-lasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

Currently there are several A II antagonists in development. Among these development candidates, is Losartan which is disclosed in a U.S. Pat. No. 5,138,069 issued to DuPont on Aug. 11, 1992. Losartan has been demonstrated to be an orally active A II antagonist, selective for the $AT_1$ receptor subtype.

Some known non-peptide antihypertensive agents act by inhibiting an enzyme, called angiotensin converting enzyme (ACE), which is responsible for conversion of angiotensin I to AII. Such agents are thus referred to as ACE inhibitors, or converting enzyme inhibitors (CEI's). Captopril and enalapril are commercially available CEI's. Based on experimental and clinical evidence, about 40% of hypertensive patients are non-responsive to treatment with CEI's. But when a diuretic such as furosemide or hydrochlorothiazide is given together with a CEI, the blood pressure of the majority of hypertensive patients is effectively normalized. Diuretic treatment converts the non-renin dependent state in regulating blood pressure to a renin-dependent state. Although the imidazoles of this invention act by a different mechanism, i.e., by blocking the AII receptor rather than by inhibiting the angiotensin converting enzyme, both mechanisms involve interference with the renin-angiotensin cascade. A combination of the CEI enalapril maleate and the diruetic hydrochlorothiazide is commercially available under the trademark Vaseretic® from Merck Co. Publications which relate to the use of diuretics with CEI's to treat hypertension, in either a diuretic-first, stepwise approach or in physical combination, include Keeton, T. K. and Campbell, W. B., Pharmacol. Rev., 31:81 (1981) and Weinberger, M. H., Medical Clinics N. America, 71:979 (1987). Diuretics have also been administered in combination with saralasin to enhance the antihypertensive effect.

Non-steroidal anti-inflammatory drugs (NSAID's) have been reported to induce renal failure in patients with renal under perfusion and high plasma level of AII. (Dunn, M. J., Hospital Practice, 19:99, 1984). Administration of an AII blocking compound of this invention in combination with an NSAID (either stepwise or in physical combination) can prevent such renal failure. Saralasin has been shown to inhibit the renal vasoconstrictor effect of indomethacin and meclofenamate in dogs (Satoh, et al., *Circ. Res.* 36/37 (Suppl. I):I-89, 1975; Blasingham, et al.,*Am J. Physiol.* 239: (F360, 1980). The CEI captopril has been demonstrated to reverse the renal vasoconstrictor effect of indomethacin in dogs with non-hypotensive hemorrhage. (Wong, et al., *J. Pharmacol. Exp. Ther*. 219:104, 1980).

Insulin resistance is defined as a reduced biological effect of insulin, and has been shown to be an independent risk factor for cardiovascular disease, and to be associated with hypertension, obesity and diabetes. Modan M, Halkin H, Almog S., et al.: Hyperinsulineamia: a link between hypertension, obesity and glucose intolerance. J. Clin Invest 1985, 75:809–817; Landberg L: Diet, obesity, and hypertension: an hypothesis involving insulin, the sympathetic nervous system, and adaptive thermogenesis. Q. J. Med. 1986, 236: 1081–1090; Ferranini E, Buzzigoli G, Giorico M A., et al.: Insulin resistance in essential hypertension. N. Engl. J. Med. 1987, 317:350–357.

Pharmacological treatment of hypertension has reduced the incidence of stroke to the level expected from epidemiological studies, but has shown considerably less of an effect on coronary heart disease. Collins R., Peto R., MacMahon S., Hebert P. Fiebach N. H., Eberlein K. A., et al. "Blood Pressure, Stroke and Coronary Heart Disease. Part 2, short term reductions in Blood pressure: overview of randomized drug trials in their epidemiological context." Lancet 1990; 9: 983–986. The reason for this is unclear, but one of the possible explanations is the use of beta-blockers and diuretics negatively influence lipid balance and insulin sensititvity. Studies of other vasodilatatory drugs, such as calcium-channel blockers, ACE-inhibitors and alpha-blockers, these drugs have been found to be neutral or improve insulin resistance. A mechanism has been suggested by Julius et al. Julius S, Gudbrandsson T, Jamerson K et al., "The hemodynamic link between insulin resistance and hypertension." J. Hypertens 1991; 9:983–986 and others, that it is possibly a hemodynamic determinator of insulin resistance.

DETAILED DESCRIPTION OF THE INVENTION

This invention relates to a novel method for the improvement of insulin sensitivity, alone or in conjunction with the treatment of hypertension, using an Angiotensin II antagonist.

This invention relates to the use of the Angiotensin II receptor antagonists as recited in European patent applications: EP 475,206, EP 497,150, EP 539,096, EP 539,713, EP 535,463, EP 535,465, EP 542,059, EP 497,121, EP 535,420, EP 407,342, EP 415,886, EP 424,317, EP 435,827, EP 433,983, EP 475,898, EP 490,820, EP 528,762, EP 324,377, EP 323,841, EP 420,237, EP 500,297, EP 426,021, EP 480,204, EP 429,257, EP 430,709, EP 434,249, EP 446,062, EP 505,954, EP 524,217, EP 514,197, EP 514,198, EP 514,193, EP 514,192, EP 450,566, EP 468,372, EP 485,929, EP 503,162, EP 533,058, EP 467,207, EP 399,731, EP 399,732, EP 412,848, EP 453,210, EP 456,442, EP 470,794, EP 470,795, EP 495,626, EP 495,627, EP 499,414, EP 499,416, EP 499,415, EP 511,791, EP 516,392, EP 520,723, EP 520,724, EP 539,066, EP 438,869, EP 505,893, EP 530,702, EP 400,835, EP 400,974, EP 401,030, EP 407,102, EP 411,766, EP 409,332, EP 412,594, EP 419,048, EP 480,659, EP 481,614, EP 490,587, EP 467,715, EP 479,479, EP 502,725, EP 503,838, EP 505,098, EP 505,111, EP 513,979, EP 507,594, EP 510,812, EP 511,767, EP 512,675, EP 512,676, EP 512,870, EP 517,357, EP 537,937, EP 534,706, EP 527,534, EP 540,356, EP 461,040, EP 540,039, EP 465,368, EP 498,723, EP 498,722, EP 498,721, EP 515,265, EP 503,785, EP 501,892, EP 519,831, EP 532,410, EP 498,361, EP 432,737, EP 504,888, EP 508,393, EP 508,445, EP 403,159, EP 403,158, EP 425,211, EP 427,463, EP 437,103, EP 481,448, EP 488,532, EP 501,269, EP 500,409, EP 540,400, EP 005,528, EP 028,834, EP 028,833, EP 411,507, EP 425,921, EP 430,300, EP 434,038, EP 442,473, EP 443,568, EP 445,811, EP 459,136, EP 483,683, EP 518,033, EP 520,423, EP 531,876, EP 531,874, EP 392,317, EP 468,470, EP 470,543, EP 502,314, EP 529,253, EP 543,263, EP 540,209, EP 449,699, EP 465,323, EP 521,768, and EP 415,594, which are incorporated by reference into the instant application.

This invention relates to the use of the Angiotensin II receptor antagonists as recited in PCT patent applications: WO 92/14468, WO 93/08171, WO 93/08169, WO 91/00277, WO 91/00281, WO 91/14367, WO 92/00067, WO 92/00977, WO 92/20342, WO 93/04045, WO 93/04046, WO 91/15206, WO 92/14714, WO 92/09600, WO 92/16552, WO 93/05025, WO 93/03018, WO 91/07404, WO 92/02508, WO 92/13853, WO 91/19697, WO 91/11909, WO 91/12001, WO 91/11999, WO 91/15209, WO 91/15479, WO 92/20687, WO 92/20662, WO 92/20661, WO 93/01177, WO 91/17771, WO 91/14679, WO 91/13063, WO 92/13564, WO 91/17148, WO 91/18888, WO 91/19715, WO 92/02257, WO 92/04335, WO 92/05161, WO 92/07852, WO 92/15577, WO 93/03033, WO 91/16313, WO 92/00068, WO 92/02510, WO 92/09278, WO 9210179, WO 92/10180, WO 92/10186, WO 92/10181, WO 92/10097, WO 92/10183, WO 92/10182, WO 92/10187, WO 92/10184, WO 92/10188, WO 92/10180, WO 92/10185, WO 92/20651, WO 93/03722, WO 93/06828, WO 93/03040, WO 92/19211, WO 92/22533, WO 92/06081, WO 92/05784, WO 93/00341, WO 92/04343, WO 92/04059, and WO 92/05044, which are incorporated by reference into the instant application.

This invention relates to the use of the Angiotensin II receptor antagonists as recited in U.S. patents: U.S. Pat. No. 5,104,877, U.S. Pat. No. 5,187,168, U.S. Pat. No. 5,149,699, U.S. Pat. No. 5,185,340, U.S. Pat. No. 4,880,804, U.S. Pat. No. 5,138,069, U.S. Pat. No. 4,916,129, U.S. Pat. No. 5,153,197, U.S. Pat. No. 5,173,494, U.S. Pat. No. 5,137,906, U.S. Pat. No. 5,155,126, U.S. Pat. No. 5,140,037, U.S. Pat. No. 5,137,902, U.S. Pat. No. 5,157,026, U.S. Pat. No. 5,053,329, U.S. Pat. No. 5,132,216, U.S. Pat. No. 5,057,522, U.S. Pat. No. 5,066,586, U.S. Pat. No. 5,089,626, U.S. Pat. No. 5,049,565, U.S. Pat. No. 5,087,702, U.S. Pat. No. 5,124,335, U.S. Pat. No. 5,102,880, U.S. Pat. No. 5,128,327, U.S. Pat. No. 5,151,435, U.S. Pat. No. 5,202,322, U.S. Pat. No. 5,187,159, U.S. Pat. No. 5,198,438, U.S. Pat. No. 5,182,288, U.S. Pat. No. 5,036,049, U.S. Pat. No. 5,140,036, U.S. Pat. No. 5,087,634, U.S. Pat. No. 5,196,537, U.S. Pat. No. 5,153,347, U.S. Pat. No. 5,191,086, U.S. Pat. No. 5,190,942, U.S. Pat. No. 5,177,097, U.S. Pat. No. 5,212,177, U.S. Pat. No. 5,208,234, U.S. Pat. No. 5,208,235, U.S. Pat. No. 5,212,195, U.S. Pat. No. 5,130,439, U.S. Pat. No. 5,045,540, U.S. Pat. No. 5,041,152, and U.S. Pat. No. 5,210,204, which are incorporated by reference into the instant application.

The method of improving of insulin sensitivity, alone or in conjunction with the treatment of hypertension using an angiotensin II receptor antagonist of formula I.

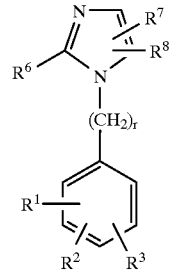

I wherein:

$R^1$ is:

4-$CO_2H$; 4-$CO_2R^9$;

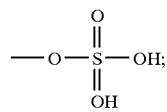

—$SO_3H$; —$C(CF_3)_2OH$;

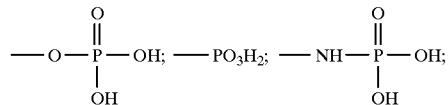

4-$NHSO_2CH_3$;

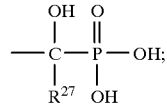

4-$NHSO_2CF_3$; —$CONHOR^{12}$; —$SO_2NH_2$;

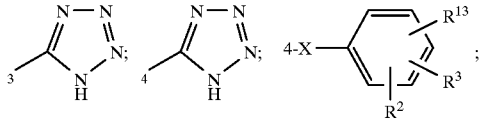

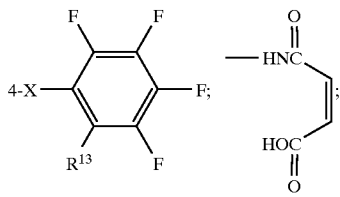

-continued

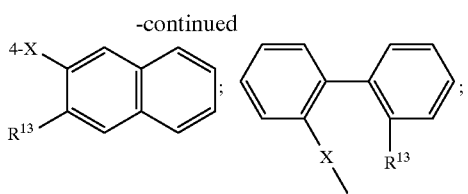

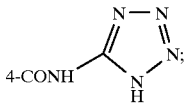

4-CONHNHSO$_2$CF$_3$;

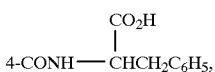

(I-isomer);

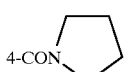 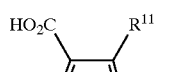

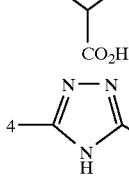

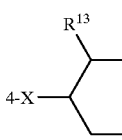

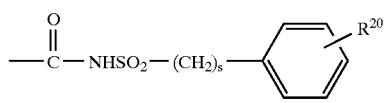

R$^2$ is H; Cl; Br; I; F; NO$_2$; CN; alkyl of 1 to 4 carbon atoms; acyloxy of 1 to 4 carbon atoms; alkoxy of 1 to 4 carbon atoms; CO$_2$H; CO$_2$R$^9$; HNSO$_2$CH$_3$; NHSO$_2$CF$_3$; CONHOR$^{12}$; SO$_2$NH$_2$;

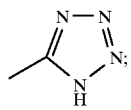

aryl; or furyl;

R$^3$ is H; Cl, Br, I or F; alkyl of 1 to 4 carbon atoms or alkoxy of 1 to 4 carbon atoms;

R$^4$ is CN, NO$_2$ or CO$_2$R$^{11}$;

R$^5$ is H, alkyl of 1 to 6 carbon atoms, cycloalkyl of 3 to 6 carbon atoms alkenyl or alkynyl of 2 to 4 carbon atoms;

R$^6$ is alkyl of 2 to 10 carbon atoms, alkenyl or alkynyl of 3 to 10 carbon atoms or the same groups substituted with F or CO$_2$R$^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms;

(CH$_2$)$_s$Z(CH$_2$)$_m$R$^5$ optionally substituted with F or CO$_2$R$^{14}$; benzyl substituted on the phenyl ring with 1 or 2 halogens, alkoxy of 1 to 4 carbon atoms, alkyl of 1 to 4 carbon atoms or nitro;

R$^7$ is H, F, Cl, Br, I, NO$_2$, C$_v$F$_{2v+1}$, where v=1–6, C$_6$F$_5$; CN;

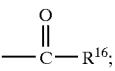

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, OCH$_3$, CF$_3$, and COOR, where R is H, alkyl of 1 to 4 carbon atoms, or phenyl;

R$^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —(CH$_2$)$_m$-imidazol-1-yl; —(CH$_2$)$_m$-1,2,3-triazolyl optionally substituted with one or two group selected from CO$_2$CH$_3$ or alkyl of 1 to 4 carbon atoms; —(CH$_2$)$_s$ tetrazolyl;

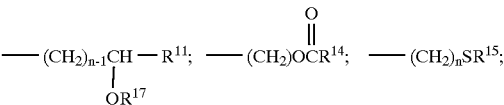

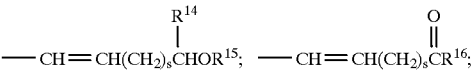

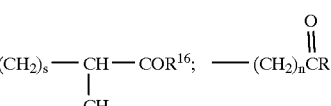

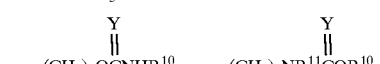

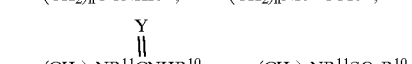

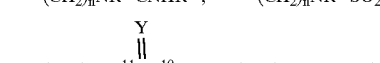

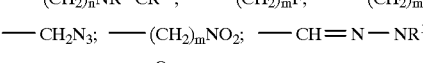

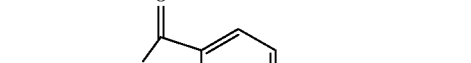

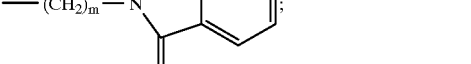

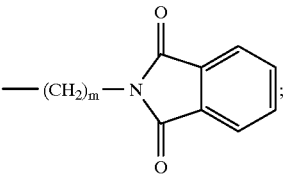

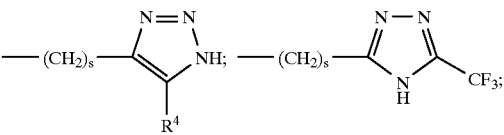

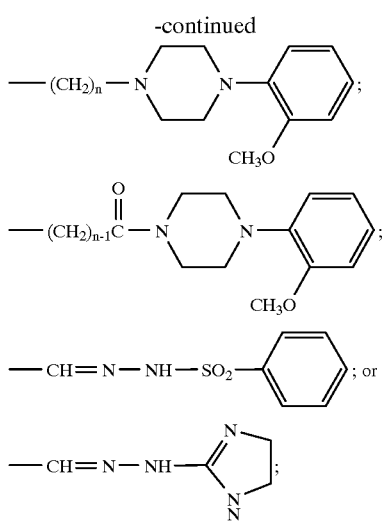

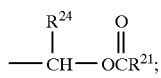

$R^9$ is:

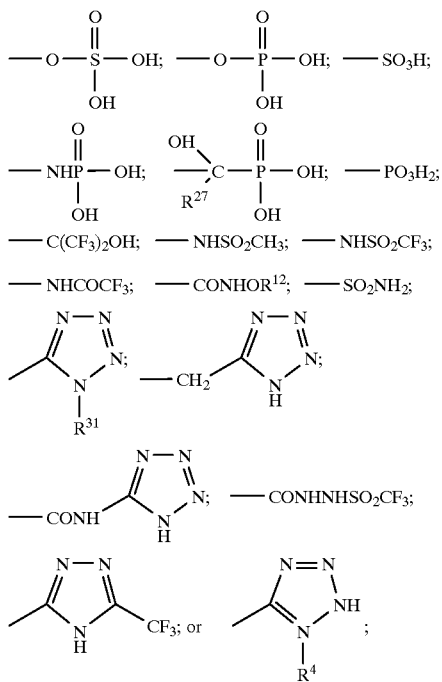

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is $—CO_2H$; $—CO_2R^9$; $—CH_2CO_2H$, $—CH_2CO_2R^9$;

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

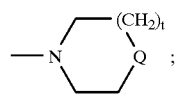

Q is $NR^{20}$, O or $CH_2$;

$R^{20}$ is H, alkyl of 1–4 carbon atoms, or phenyl;

$R^{21}$ is alkyl of 1 to 6 carbon atoms, $—NR^{22}R^{23}$, or

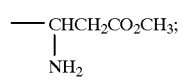

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $—C_6H_5$;

$R^{25}$ is $NR^{27}R^{28}$, $OR^{28}$, $NHCONH_2$, $NHCSNH_2$,

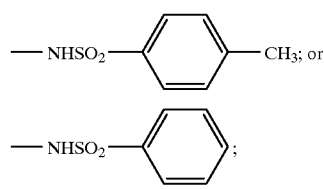

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $—(CH_2)_q—$;

$R^{31}$ is H, alkyl or 1 to 4 carbon atoms, $—CH_2CH=CH_2$ or $—CH_2C_6H_4R^{32}$;

X is a carbon-carbon single bond, $—CO—$, $—CH_2—$, $—O—$, $—S—$, $—NH—$,

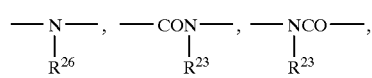

$—OCH_2—$, $—CH_2O—$, $—SCH_2—$, $—CH_2S—$,
$—NHC(R^{27})(R^{28})—$, $—NR^{23}SO_2—$, $—SO_2NR^{23}—$,
$—CH=CH—$, $—CF=CF—$, $—CH=CF—$,
$—CF=CH—$, $—CH_2CH_2—$, $—C(R^{27})(R^{28})NH—$,

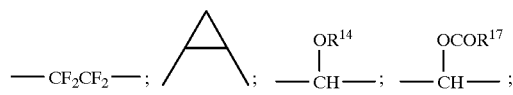

-continued

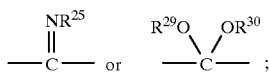

Y is O or S;

Z is O, $NR^{11}$, or S;

m is 1 to 5;

n is 1 to 10;

p is 0 to 3;

q is 2 to 3;

r is 0 to 2;

s is 0 to 5;

t is 0 or 1;

and pharmaceutically acceptable salts of these compounds; provided that:

(1) the $R^1$ group is not in the ortho position;

(2) when $R^1$ is

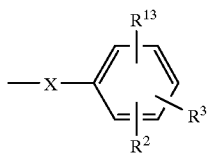

X is a single bond, and $R^{13}$ is $CO_2H$, or

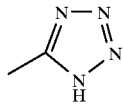

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

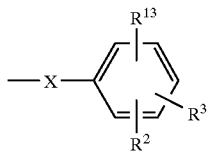

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

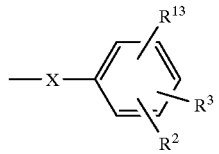

X is —$OCH_2$—, and $R^{13}$ is 2-$CO_2H$, and $R^7$ is H then $R^6$ is not $C_2H_5S$;

(7) when $R^1$ is

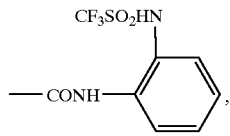

and $R^6$ is n-hexyl then $R^7$ and $R^8$ are not both hydrogen;

(8) when $R^1$ is

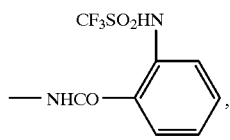

$R^6$ is not methoxybenzyl;

(9) the $R^6$ group is not

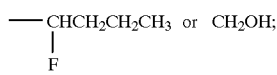

or $CH_2OH$;

(10) when r=0, $R^1$ is

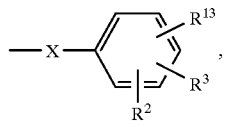

X is

$R^{13}$ is 2-$NHSO_2CF_3$, and $R^6$ is n-propyl, then $R^7$ and $R^8$ are not —$CO_2CH_3$;

(11) when r=0, $R^1$ is:

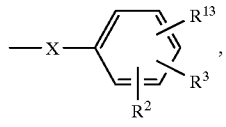

X is $$-NH-\overset{O}{\underset{\|}{C}}-,$$

$R^{13}$ is 2-COOH, and $R^6$ is n-propyl, then $R^7$ and $R^8$ are not —$CO_2CH_3$;

(12) when r=1, $R^1$ is:

$$-X-\left\langle\begin{array}{c}R^{13}\\R^3\\R^2\end{array}\right\rangle,$$

X is a single bond, $R^7$ is Cl, and $R^8$ is —CHO, then $R^{13}$ is not 3-(tetrazol-5-yl);

(13) when r=1, $R^1$ is:

$$-X-\left\langle\begin{array}{c}R^{13}\\R^3\\R^2\end{array}\right\rangle,$$

X is a single bond, $R^7$ is Cl, and $R^8$ is —CHO, then $R^{13}$ is not 4-(tetrazol-5-yl).

Preferred for the improvement of insulin sensitivity alone or in conjunction with the treatment of hypertension are the compounds having the formula:

[imidazole structure with $R^6$, $R^7$, $R^8$, $CH_2$, phenyl, $R^1$]

wherein:

$R^1$ is —$CO_2H$; —$NHSO_2CF_3$;

[tetrazolyl structure]; —X—[phenyl with $R^{13}$, $R^2$];

or [biphenyl structure with X, $R^{13}$];

$R^6$ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, and nitro;

$R^8$ is phenylalkenyl wherein the aliphatic portion is 2 to 4 carbon atoms, —$(CH_2)_m$-imidazol-1yl, —$(CH_2)_m$1,2,3-triazolyl optionally substituted with one or two groups selected from $CO_2CH_3$ or alkyl of 1 to 4 carbon atoms, $(CH_2)_m$-tetrazolyl, —$(CH_2)_nOR^{11}$; —$(CH_2)_n\overset{O}{\underset{\|}{O}}CR^{14}$;

—$CH=CH(CH_2)_s\overset{O}{\underset{\|}{C}}R^{16}$, —$CH=CH(CH_2)_s\overset{R^{14}}{\underset{|}{C}}HOR^{15}$;

—$(CH_2)_n\overset{O}{\underset{\|}{C}}R^{16}$; —$(CH_2)_n NH\overset{O}{\underset{\|}{C}}R^{10}$;

—$(CH_2)_n NHSO_2R^{10}$; —$(CH_2)_mF$; —$\overset{O}{\underset{\|}{C}}R^{16}$;

$R^{13}$ is —$CO_2H$, —$CO_2R^9$, $NHSO_2CF_3$; $SO_3H$;

or [tetrazolyl structure];

$R^{16}$ is H, alkyl of 1 to 5 carbon atoms, $OR^{17}$, or $NR^{18}R^{19}$;

X is carbon-carbon single bond, —CO—,

—$\underset{R^{23}}{CON}$—, —$CH_2CH_2$—, —$\underset{R^{23}}{NCO}$—,

—$OCH_2$—, —$CH_2O$—, —$SCH_2$—, —$CH_2S$—, —$NHCH_2$—, —$CH_2NH$— or —CH=CH—; and pharmaceutically acceptable salts of these compounds.

More preferred the improvement of insulin sensitivity alone or in conjunction with the treatment of hypertension are compounds of the preferred scope wherein:

$R^2$ is H, alkyl of 1 to 4 carbon atoms, halogen, or alkoxy of 1 to 4 carbon atoms;

$R^6$ is alkyl, alkenyl or alkynyl of 3 to 7 carbon atoms;

$R^7$ is H, Cl, Br, $C_vF_{2v+1}$, where v=1–3, or

—$\overset{O}{\underset{\|}{C}}R^{16}$;

$R^8$ is —$(CH_2)_mOR^{11}$; —$(CH_2)_m\overset{O}{\underset{\|}{O}}CR^{14}$;

—$CH=CH-\overset{R^{14}}{\underset{|}{C}}HOR^{15}$; —$(CH_2)_m\overset{O}{\underset{\|}{C}}R^{16}$;

—$CH_2NH\overset{O}{\underset{\|}{C}}R^{10}$; —$(CH_2)_m NHSO_2R^{10}$;

-continued

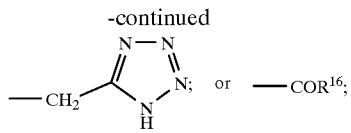

$R^{10}$ is $CF_3$, alkyl of 1 to 6 carbon atoms or phenyl;
$R^{11}$ is H, or alkyl of 1 to 4 carbon atoms;
$R^{13}$ is $CO_2H$; $CO_2CH_2OCOC(CH_3)_3$; $NHSO_2CF_3$; and

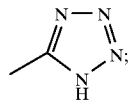

$R^{14}$ is H, or alkyl of 1 to 4 carbon atoms;
$R^{15}$ is H, alkyl of 1 to 4 carbon atoms, or acyl of 1 to 4 carbon atoms;
$R^{16}$ is H, alkyl of 1 to 5 carbon atoms; $OR^{17}$; or

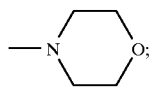

m is 1 to 5;
X is single bond, —O—; —CO—; —NHCO—; or —OCH$_2$—; and pharmaceutically acceptable salts.
Specifically preferred for their activity in this method of use are:
2-Butyl-4-chloro-1-[(2'-(1H-tetrazol-5-yl)biphenyl-4-yl)methyl]-5-(hydroxymethyl)imidazole.
2-Butyl-4-chloro-1-[(2'-carboxybiphenyl-4-yl)methyl]-5-(hydroxymethyl)imidazole.
2-Butyl-4-chloro-1-[(2'-carboxybiphenyl-4-yl)methyl]-5-[(methoxycarbonyl)aminomethyl]imidazole.
2-Butyl-4-chloro-1-[(2'-carboxybiphenyl-4-yl)methyl]-5-[(propoxycarbonyl)aminomethyl]imidazole.
2-Butyl-4-chloro-1-[(2'-carboxybiphenyl-4-yl)methyl]imidazole-5-carboxaldehyde.
2-Butyl-1-[(2'-carboxybiphenyl-4-yl)methyl]-imidazole-5-carboxaldehyde.
2-(1E-Butenyl)-4-chloro-1-[(2'-carboxybiphenyl-4-yl)methyl]-5-(hydroxymethyl)imidazole.
2-(1E-Butenyl)-4-chloro-1-[(2'-carboxybiphenyl-4-yl)methyl]-imidazole-5-carboxaldehyde.
2-Propyl-4-chloro-1-[(2'-(1H-tetrazol-5-yl)biphenyl-4-yl)methyl]-5-(hydroxymethyl)imidazole.
2-Propyl-4-chloro-1[(2'-(1H-tetrazol-5-yl)biphenyl-4-yl)methyl]-imidazole-5-carboxaldehyde.
2-Butyl-4-chloro-1-[2'-(1H-tetrazol-5-yl)biphenyl-4-yl)methyl]-imidzole-5-carboxaldehyde.
2-(1E-Butenyl)-4-chloro-1-[(2'-(1H-tetrazol-5-yl)biphenyl-4-yl)methyl]-5-hydroxymethyl)imidazole.
2(1E-Butenyl)-4-chloro-1-[(2'-(1H-tetrazol-5-yl)biphenyl-4-yl)methyl]imidazole-5-carboxaldehyde.
2-Butyl-4-chloro-1-[(2'-(1H-tetrazol-5-yl)-biphenyl-4-yl)methyl]-imidazole-5-carboxylic acid.
2-Propyl-4-chloro-1-[(2'-(1H-tetrazol-5-yl)-biphenyl-4-yl)methyl]-imidazole-5-carboxylic acid.
2-Propyl-4-trifluoromethyl-1-[(2'-(1H-tetrazol-5-yl)biphenyl-4-yl)methyl]imidazole-5-carboxylic acid.
2-Propyl-4-trifluoromethyl-1-[(2'-(1H-tetrazol-5-yl)biphenyl-4-yl)methyl]-5-(hydroxylmethyl)imidazole.
2-Butyl-4-trifluoromethyl-1-[(2'-(1H-tetrazol-5-yl)biphenyl-4-yl)methyl]imidazole-5-carboxylic acid.
2-Propyl-4-trifluoromethyl-1-[(2'-(carboxybiphenyl-4-yl)methyl]-imidazole-5-carboxaldehyde.
2-Propyl-4-pentafluoroethyl-1-[(2'-(1H-tetrazol-5-yl)biphenyl-4-yl)methyl]-5-(hydroxymethyl)imidazole.
2-Propyl-1-[(2-(1H-tetrazol-5-yl)biphenyl-4-yl)methyl]imidazole-4,5,-dicarboxylic acid.
2-Propyl-4-pentafluoroethyl-1-[(2'-(1H-tetrazol-5-yl)biphenyl-4-yl)methyl]imidazole-5-carboxylic acid.
2-Propyl-4-pentafluoroethyl-[(2'-(1H-tetrazol-5-yl)biphenyl-4-yl)methyl]imidazole-5-carboxaldehyde,
or a pharmaceutically acceptable salt thereof.

The most preferred compounds for the improvement of insulin sensitivity alone or in conjunction with the treatment of hypertension are:

2-Butyl-4-chloro-1-[(2'-tetrazol-5-yl)biphenyl-4-yl]methyl]-5-(hydroxymethyl)imidazole; and
2-Butyl-4-chloro-1-[(2'-tetrazol-5-yl)biphenyl-4-yl]methylimidazole-5-carboxylic acid or a pharmaceutically acceptable salt thereof.

A further aspect of the invention is the use of an angiotensin II receptor antagonist, especially a substituted imidazole of formula I, for the preparation of a medicament for the improvement of insulin sensitivity alone, or in conjunction with the treatment of hypertension.

Note that throughout the text when an alkyl substituent is mentioned, the normal alkyl structure is meant (i.e., butyl is n-butyl) unless otherwise specified.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention is a method for the improvement of insulin sensitivity alone or in conjunction with the treatment of hypertension using pharmaceutical compositions comprising a suitable pharmaceutical carrier and a compound of Formula (I). The pharmaceutical compositions which contain one or more other therapeutic agents, such as a diuretic or a non-steroidal anti-inflammatory drug.

It should be noted in the foregoing structural formula, when a radical can be a substituent in more than one previously defined radical, that first radical can be selected independently in each previously defined radical. For example, $R^1$, $R^2$ and $R^3$ can each be $CONHOR^{12}$. $R^{12}$ need not be the same substituent in each of $R^1$, $R^2$ and $R^3$ but can be selected independently for each of them.

SYNTHESIS

The novel compounds of Formula (I) may be prepared using the reactions and techniques described in U.S. Pat. No. 5,138,069 and WO 93/10106 or one of its three U.S. counterparts, U.S. Pat. No. 5,130,439 issued Jul. 14, 1992, U.S. Pat. No. 5,206,374 issued Apr. 27, 1993, and U.S. Ser. No. 07/911,813 filed Jul. 10, 1992.

EXAMPLE 1

Losartan [DUP 753]

Step A: Preparation of 4'-methylbiphenyl-2-carboxylic acid
Methyl 4'-methylbiphenyl-2-carboxylate (10.0 g, 44.2 mmol, 1 eq), 0.5 N KOH in methanol (265.5 mL, 133 mmol, 3 eq), and water (50 mL) were mixed and refluxed under $N_2$. After 5 hours, the solvent was removed in vacuo and water (200 mL) and ethyl acetate (200 mL) added. The aqueous layer was acidified with concentrated hydrochloric acid to a pH of 3 and the layers were separated. The aqueous phase was extracted with ethyl acetate (2×200 mL), the organic layers collected, dried (MgSO$_4$) and the solvent removed in vacuo to yield 8.71 g of a white solid; m.p. 140.0°–145.0°. NMR (200 MHz, DMSO-d$_6$) δ 7.72 (d, 1H, J=7 Hz); 7.56 (t, 1H, J=7 Hz); 7.45 (d, 1H, J=7 Hz); 7.40 (t, 1H, J=7 Hz); 7.25 (s, 4H); 2.36 (s, 3H). Anal Calcd. for C$_{14}$H$_{12}$O$_2$; C, 79.23; H, 5.70. Found: C, 79.22; H, 5.47.

Step B: Preparation of 4'-Methyl-2-cyanobiphenyl

4'-Methylbiphenyl-2-carboxylic acid (8.71 g, 41 mmol, 1 eq) and thionyl chloride (30.0 mL, 411 mmol, 10 eq) were mixed and refluxed for 2 hours. The excess thionyl chloride was removed in vacuo and the residue was taken up in toluene. The toluene was removed by rotary evaporation and this toluene evaporation procedure was repeated to ensure that all of the thionyl chloride was removed. The crude acid chloride was then added slowly to cold (0° C.) concentrated NH$_4$OH (50 mL) so that the temperature was kept below 15°. After 15 minutes of stirring, water (100 mL) was added and solids precipitated. These were collected, washed well with water and dried under high vacuum over P$_2$O$_5$ in a dessicator overnight to yield 7.45 g of white solid; m.p. 126.0°–128.5°. NMR (200 MHz, DMSO-d$_6$) δ 7.65–7.14 (m, 10H), 2.32 (s, 3H). Anal Calcd. for C$_{14}$H$_{13}$NO: C, 79.59; H, 6.20; N, 6.63. Found C, 79.29; H, 6.09; N, 6.52.

The above product amide (7.45 g, 35 mmol, 1 eq) and thionyl chloride (25.7 mL, 353 mmol, 10 eq) were mixed and refluxed for 3 hours. The thionyl chloride was removed using the same procedure as described above. The residue was washed with a little hexane which partly solubilized the product, but removed the impurity as well to yield 6.64 g of white solid; m.p. 44.0°–47.0°. NMR (200 MHz, DMSO-d$_6$) δ 7.95 (d, 1H, J=8 Hz); 7.78 (t, 1H, J=7 Hz); 7.69–7.32 (m, 6H); 2.39 (s, 3H). Anal Calcd. for C$_{14}$H$_{11}$N: C, 87.01; H, 5.74. Found C, 86.44; H, 5.88.

Step C: Preparation of 4'-bromomethyl-2-cyanobiphenyl

A solution of 5.59 g of 4'-methyl-2-cyanobiphenyl, 29 mmol of N-bromosuccinimide, 0.9 mmol of benzoylperoxide and 500 mL of carbon tetrachloride was refluxed for 3 hours. After cooling to room temperature, the resulting suspension was filtered and then concentrated in vacuo to provide the crude 4'-bromomethyl-2-cyanobiphenyl. The product was recrystallized from ether to yield 4.7 g of product; m.p. 114.5°–120.0°. NMR (200 MHz, CDCl$_3$) δ 7.82–7.37 (m, 8H); 4.50 (s, 2H). Anal. Calcd. for C$_{14}$H$_{10}$BrN: C, 61.79, H, 3.70; N, 5.15. Found: C, 62.15; H, 3.45; N, 4.98.

Step D: Preparation of 2-n-butyl-4-chloro-1-[2'-cyanobiphenyl-4-yl)methyl]5-(hydroxymethyl)-imidazole To a suspension of 1.43 g of sodium methoxide in 20 mL of dimethylformamide at 25° was added a solution of 15.3 mmol of 2-butyl-4(5)-chloro-5(4)-hydroxymethyl imidazole (prepared as described in U.S. Pat. No. 4,355,040) in 15 mL of DMF. The resulting mixture was stirred at 25° for 0.25 hours, and then to this mixture 4.6 g, 16.9 mmol of 4'bromomethyl-2-cyanobiphenyl in 15 mL of DMF. Finally, the reaction mixture was stirred at 40° for 4 hours. After cooling to 25°, the solvent was removed in vacuo. The residue was dissolved in 1:1 hexane/ethyl acetate, and this solution was washed with water and brine, dried over anhydrous sodium sulfate, filtered, and concentrated. The crude product contains two regioisomers, the faster moving one by TLC being the more potent isomer. Flash chromatography in 1:1 hexane/ethyl acetate over silica gel to separate the regioisomeric products yielded 2.53 g of the faster eluting isomer. Recrystallization from acetonitrile yielded 1.57 g of analytically pure product; m.p. 153.5°–155.5°. NMR (200 MHz, CDCl$_3$) δ 7.82–7.43 (m, 6); 7.12 (d, 2, J=8 Hz); 5.32 (s, 2); 4.52 (s, 2); 2.62 (t, 2, J=7 Hz); 1.70 (t of t, 2, J=7.7 Hz); 1.39 (t of q, 2, J=7,7 Hz); 0.90 (t, 3, J=7 Hz). Anal. Calcd. for C$_{22}$H$_{22}$ClN$_3$O: C, 69.56; H, 5.84; N, 11.06. Found: C, 69.45; H, 5.89; N, 10.79.

Step E: Preparation of 2-n-butyl-4-chloro-5-hydroxymethyl-1-[(2'-(1H-tetrazol-5-yl)biphenyl-4-yl)methyl]imidazole 2-n-Butyl-4-chloro-1-[(2'-cyanobiphenyl-4-yl)-methyl]-5-(hydroxymethyl)imidazole (11.93 g, 1.0 eq), sodium azide (3 eq), and ammonium chloride (3 eq) were mixed and stirred in DMF (150 mL) in a round bottom connected to a reflux condenser under N$_2$. An oil bath with a temperature controller was then used to heat the reaction at 100° C. for 2 days, after which the temperature was raised to 120° C., for 6 days. The reation was cooled and 3 more equivalents of ammounium chloride and sodium azide were added. The reaction was again heated for 5 more days at 120° C. The reaction was cooled, the inorganic salts filtered, and the filtrate solvent removed in vacuo. Water (200 mL) and ethyl acetate (200 mL) were added to the residue and the layers were separated. The aqueous layer was extracted with ehtyl acetate (2×200 mL), the organic layers were collected, dried (MgSO$_4$) and the solvent removed in vacuo, to yield a dark yellow oil. The product was purified by flash chromatography in 100% ethyl acetate to 100% ethanol over silica gel to yield 5.60 g of a light yellow solid. Recrystallization from acetonitrile yielded 4.36 g of light yellow crystals which still melted broadly. The crystals were taken up in 100 mL of hot acetonitrile. The solid that did not dissolve was filtered off to yield 1.04 g of product as a light yellow solid; m.p. 183.5°–184.5°. Upon cooling, the mother liquor yielded an additional 1.03 g of product as a light yellow solid; m.p. 179.0°–180.0°. NMR (200 MHz, DMSO-d$_6$) δ 7.75–7.48 (m, 4H); 7.07 (d, 2H, J=9 Hz); 7.04 (d, 2H, J=9 Hz); 5.24 (s, 2H); 5.24 (bs, 1H); 4.34 (s, 2H); 2.48 (t, 2H, J=7 Hz); 1.48 (t of t, 2H, J=7,7 Hz); 1.27 (t of q, 2H, J=7,7 Hz); 0.81 (t, 3H, J=7 Hz). Anal. Calcd. for C$_{22}$H$_{23}$ClN$_6$O: C, 62.48; H, 5.48; Cl, 8.38. Found for the solids which did not dissolve in 100 mL of acetonitrile: C, 62.73; H, 5.50; Cl, 8.26. Found for the solids obtained from the mother liquor: C, 62.40; H, 5.23; Cl, 8.35.

EXAMPLE 2

2-butyl-1-[2'-(1H-tetrazol-5-yl)-biphenyl-4-yl) methyl]-4-chloroimidazole-5-carboxylic acid (EXP-3174)

A mixture of 2-butyl-5-hydroxymethyl-4-chloro-1-[2'-triphenylmethyltetrazol-5-yl)-biphenyl-4-yl)methyl] imidazole and activated manganese dioxide in 50 mL of methylene chloride was stirred at 25° C. At 24 hours into the reaction 2.00 g of manganese dioxide was added. After a total of 100 hours the reaction mixture was filtered with methylene chloride. The solids then were washed with methanol, and the methanol filtrate concentrated. The residue was dissolved in water. The resulting aqueous solution was adjusted to pH 3 using 10% hydrochloric acid and then extracted with 4:1 chloroform/i-propanol. The combined organic phases were washed with brine, dried over anhydrous sodium sulfate, filtered, and concentrated. Column chromatography (elution(95:5:0.5 chloroform/methanol/ acetic acid) furnished 2-butyl-1-[(2'-(1H-tetrazol-5-yl)-biphenyl-4-yl)methyl]-4-chloroimidazole-5-carboxylic acid as an amorphous solid. NMR (200 MHz, DMSO-d$_6$): δ 7.46–7.63 (m, 4H), 7.05 (d, 2H, J=8 Hz), 6.93 (d, 2H, J=8 Hz), 5.56 (s, 2H), 4.10 (s, 12H), 2.55 (t, 2H, J=7.5 Hz), 1.44–1.52 (m, 2H), 1.17–1.28 (m, 2H), 0.78 (t, 3H, J=7 Hz).

EXAMPLE 3

Step A: 2-(2'-Triphenylmethyl-2'H-tetrazol-5'-yl)phenylboronic acid

Alternative 1

To a 22 L flask under nitrogen purge was charged 8.25 L acetone, followed by 1.1 kg 5-phenyltetrazole. Triethylamine (800 g) was added in such a rate that the temperature was maintained below 35° C. with some cooling. Solid trityl chloride was charged to this light suspension in five 440 g portions. The temperature was maintained below 35° C. An additional 1.38 L acetone was added to the reaction which was then maintained at 25° to 30° C. with stirring for 2 hours. Water (2.2 L) was added and the mixture was chilled to 15° to 20° C. The solid was collected by filtration; the filter cake was rinsed with 1.65 L 50% acetone-water followed by excess amount of water. The wet cake was re-slurried in 8 L acetone and 8 L of water was added slowly. The suspension was stirred for 1 hour then filtered. The filter cake was rinsed with 3 to 5 L of water. The white solid was dried in a vacuum oven at 40–45° C. to a constant weight of 3.0 kg, mp 158–160° C.

To a dry 12 L flask under nitrogen purge was charged 3.19 L of dry tetrahydrofuran (THF). With agitation, 398 g of 5-phenyl-2-trityl-tetrazole prepared above was charged. The system was evacuated and released to nitrogen three times and then cooled to −20° C. A solution of butyl lithium in heptane (1.6 M, 477 g) was then added to the reaction mixture while maintaining the temperature at −15° C. to −20° C. The resultant deep red solution was stirred at −5° C. for 1 hour during which time the lithium salt crystallized out. The solid suspension was cooled to −25° C. again and 333 g triisopropylborate was charged at a temperature range of −20° to −25° C. After the addition, the mixture was allowed to warm to 20° C. without heating. About 2.5 L of solvent was removed by vacuum distillation. The pot temperature was kept below 40° C. To the mixture was then added 2.66 L of 3% acetic acid in water and the resultant suspension was stirred for 1 hour. The white solid was collected by filtration. The solid cake was rinsed with 1.5 L of 20% tetrahydrofuran in water, followed by 3 L of water. The solid was dried under vacuum at room temperature to a constant weight of 502.3 g, mp 142–146° C. (dec.).

Alternative 2

A preferred alternative procedure for preparing the title compound of this Example 1 is by means of the following procedure.

5-Phenyltetrazole (14.6 g, 100 mmol) was suspended in dry THF (120 ml) under nitrogen and triethylamine (14.8 ml, 105 mmol) was added while maintaining the temperature at 15 to 20° C. Triphenylchloromethane (29.3 g, 105 mmol) in dry THF (60 ml) was then added slowly to the mixture at ≦25° C. After the addition was complete the mixture was warmed to 35° C. for 1 hour and then cooled at 0° C. for 1 hour. The precipitated triethylammonium chloride was filtered and the filtrate was degassed via vacuum/nitrogen purges (3×). The degassed solution was cooled to −20° C. and butyllithium (1.6 M in hexanes) was added until a pink color persisted for 2 minutes. The pink color indicated that the solution was completely dry. More butyllithium (65.6 ml, 105 mmol) was charged at ≦−15° C. The deep red heterogeneous mixture was aged at −20 to −15° C. for 1 hour and triisopropylborate (30.6 ml, 130 mmol) was added while maintaining the temperature at ≦−15° C.

The deep red solution was aged at −15° C. for 30 minutes and then warmed to 10° C. over 1 hour. The mixture volume was reduced by ~200 ml in vacuo at ≦15° C. at which time <5% of hexanes (vs THF) remained. The residue was diluted with THF to a total volume of 160 ml and isopropanol (60 ml) was added. The solution was cooled to 0° C. and saturated aqueous ammonium choride (40 ml, 200 mmol) was charged within 15 minutes. The mixture was aged at 20 to 25° C. for 30 minutes and water (100 ml) was added over 30 to 45 minutes. After aging the mixture for 1 hour, the crystallized product was collected by filtration and washed with cold 80% aqueous isopropanol. The filter cake was air dried on the filter to give 69.7 g (86% yield, corrected for 82% purity) of product as the THF mono-solvate.

Step B: 2-n-butyl-4-chloro-5-hydroxymethyl-1-p-bromobenzyl-1H-imidazole

A suspension of 2-n-butyl-4-chloro-1H-imdazole-5-carboxyaldehyde (146.9 g, 0.78 mol) and p-bromobenzyl bromide (195 g, 0.79 mol) in dimethylacetamide (1.0 L) was cooled to 0° C. and potassium carbonate (1.38 g, 1.0 mol) was added. The mixture was aged for three hours at 0° C. and then at 20 to 25° C. or two to four hours. The mixture was diluted with dimethylacetamide (0.15 L) and then filtered. The filter cake was washed with dimethylacetamide (50 ml). The combined filtrates were diluted with methanol (0.66 L) and cooled to 0° C. Sodium borohydride (37.8 g, 1.0 mol) was added as a solid and the mixture was aged with stirring at 20 to 25° C. for two hours. Water (1.56 L) was added slowly to crystallize the product. The filter cake was washed carefully with water (1.56 L) and dried in vacuo at 60° C. The yield was 255 g (91%, corrected for 99.5% purity).

Step C: 2-n-butyl-4-chloro-1-[(2'-(2-triphenylmethyl-2H-tetrazol-5-yl)-1,1'-biphenyl-4-yl)methyl]1H-imidazole-5-methanol All operations described for this example were performed under an atmosphere of nitrogen.

Catalyst Preparation

To a mixture of palladium chloride (10.6 mg) and triphenylphosphine (31.5 mg) was added anhydrous toluene (4 ml). The heterogeneous solution was degassed by vacuum/nitrogen purges (3×) and then heated to 60° C. for 30 minutes. Triisopropylphosphite (30.0 microliters) was added and the mixture was further heated at 60° C. until a homogeneous solution was obtained (1 to 2 hours).

Coupling 2-(2'-triphenylmethyl-2'H-tetrazol-5'-yl)phenylboronic acid of Example 3, Step A (1.3 g) was suspended in toluene (4 ml) and water (100 microliters) was added. The heterogeneous mixture was stirred at room temperature for 30 minutes and potassium carbonate (0.7 g) was then charged followed by the titled product of Example 3, Step B (0.7 g). The mixture was degassed via vacuum/nitrogen purges (3×) and the above catalyst solution was added. The temperature of the mixture was raised 80 to 85° C. and kept at this temperature for 2 hours. After the mixture was cooled to 40° C., water (5 ml) was added. The aqueous layer was removed and the organic phase was concentrated in vacuo at ≦30° C. to a volume of ~3 ml. Methyl i-butyl ketone (MIBK) (8 ml) was added and the mixture was again reduced to ~3 ml. The mixture was diluted with MIBK (4 ml) and water (36 microliters), heated to 60° C. and then cooled and aged first at 0° C. for 30 minutes followed by aging at −10° C. with stirring for 2 hours. The crystallized product was collected by filtration as a mono-MIBK solvate (1.44 g, 94% yield). The crude product was dissolved in MIBK (2.1 ml) at 80° C., the solution was filtered hot at 80° C. and water (33.8 microliters) was added. The solution was cooled slowly to 0° C. over 1 hour and aged at 0° C. for 30 minutes followed by aging at −10° C. with stirring for 2 hours. After filtration 1.38 g of the mono-MIBK solvated product was recovered (90% yield).

EXAMPLE 4

2-n-Butyl-4-chloro-1-[(2'-(2-triphenylmethyl-2H-tetrazol-5-yl)-1,1'-biphenyl-4-yl)methyl]-1H-imidazole-5-methanol All operations described for this example were performed under an atmosphere of nitrogen.

Step A: Catalyst Preparation

The following two procedures can be used with similar results.

Alternative Procedure 1

To a mixture of palladium chloride (354 mg) and triphenylphosphine (2.1 g) was added anhydrous tetrahydrofuran (THF) (75 ml). The heterogeneous solution was degassed by vacuum/nitrogen purges (3×) and then refluxed for 4 hours. Most of the palladium chloride changed over to bis(triphenylphosphine)palladium chloride during the reflux. Some insoluble black solids were still observed at this point.

The heterogeneous THF solution containing the phosphinated palladium chloride was cooled to room temperature and diethylzinc (4.0 ml, 1 M in hexanes) was added. Except for a small amount of black solids, the solution essentially became homogeneous after stirring for 30 minutes. This activated catalyst solution was used in the coupling step described below.

Alternative Procedure 2

To a mixture of palladium chloride (354 mg) and triphenylphosphine (2.1 g) was added anhydrous THF (75 ml). The heterogeneous solution was degassed by vacuum/nitrogen purges (3×) and then triisopropylphosphite (0.99 ml) was added. The mixture was maintained at room temperature until all the palladium chloride was dissolved and a homogeneous solution was obtained (0.5 to 1 hour).

Step B: Benzyltrimethylammonium Carbonate Preparation

To a benzyltrimethylammonium hydroxide solution (42 g) was added ammonium carbonate (5.0 g) and the reaction was aged with stirring until all of the ammonium carbonate dissolved (~30 minutes). The methanol solvent was removed in vacuo and further displaced with THF (3×10 ml). The residual carbonate was dissolved in THF (90 ml).

Step C: Coupling Step

To the carbonate solution prepared in Example 4, Step B was charged the titled product of Example 3 (24.0 g) and the titled product of Example 3, Step B (14.2 g). The mixture was degassed by vacuum/nitrogen purges (5×), followed by the addition of the catalyst solution prepared as recited in Example 4, Step A (procedure 1 or 2),. The reaction mixture was heated to reflux, aged until completion (8 to 10 hours), cooled to room temperature and filtered through a pad Celite. The Celite was further washed with THF (3×10 ml). The yield was 89 wt %.

EXAMPLE 5

2-n-Butyl-4-chloro-1-[(2'-(tetrazol-5-yl)-1,1'-biphenyl-4-yl)methyl]-1H-imidazole-5-methanol potassium salt 2-n-butyl-4-chloro-1-[(2'-2-triphenylmethyl-2H-tetrazol-5-yl)-1,1'-biphenyl-4-yl)methyl]-1H-imidazole-5-methanol (5.0 g, 6.54 mmol) was dissolved in THF (60 ml). 4 N Sulfuric acid (38 ml, 152 mmol) was added with stirring at 25 to 30° C. The solution was aged overnight at 20 to 25° C. and isopropyl acetate (60 ml) was then added. The layers were separated and the organic phase was back-extracted with 4 N sulfuric acid (19 ml). The aqueous layers were combined and the organic solvents (THF and isopropyl actate) were removed in vacuo. The remaining aqueous solution was diluted with THF (10% of THF by volume) and passed through a pad of Ecosorb S 402 (5.0 g). The pad was rinsed with 10% THF in 4 N sulfuric acid. The filtrate was then passed through a column of SP-207 (60 ml) and the column was washed with water (180 ml) followed with 1 M K$_2$HPO$_4$ (180 ml). The pH of the eluent was monitored to ensure complete potassium salt formation. Further washing with water (180 ml) removed the sulfate and excess phosphate. The potassium salt product was eluted with 20% aqueous THF. Concentration of the aqueous solution and dilution with isopropanol gave crystalline product. Alternatively, the product was isolated by spray drying. The yield was 2.56 g (85%).

EXAMPLE 6

1-Bromo-4-(2'-n-butyl-4'-chloro-5'-hydroxymethylimidazole-1'H-1'-yl)methylbenzene Step A: Alkylation To 200 mL of dimethyl acetamide under a nitrogen atmosphere in a 1-liter 3-necked flask fitted with a mechanical stirrer and thermocouple is charged 30.8 g (0.163 mol) of 2-n-butyl-4-chloro-5-formyl-1H-imidazole and 43.7 g (0.16 mol) of 4-bromobenzyl bromide. The solution is cooled to −5° C. followed by portionwise addition of 27.1 g (0.19 mol) of powdered potassium carbonate over 10 min with rapid stirring while keeping the reaction temperature between −5–0° C. The slurry is stirred at −5° C. for 2 h and room temperature for 2 h or until the alkylation is complete.

Step B: Filtration

The slurry is filtered and the cake is washed with an anhydrous mixture of dimethyl acetamide (30 mL) and methanol (130 mL). The filtrate is used directly in the next step.

Step C: Reduction

Under a nitrogen atmosphere, 1.85 g (48 mmol) of powdered sodium borohydride is added portionwise over 0.5 h to the filtrate at −15° C. in a 5-liter 3-necked flask with a mechanical stirrer and a thermocouple, keeping the reaction temperature between −15 to −5° C. The mixture is warmed to room temperature and aged for 1 h or until the reduction is complete.

Step D: Crystallization

Acetic acid (2.74 mL) is added dropwise over 10 min with rapid stirring while keeping the temperature of the mixture at 20–25° C. This mixture is aged at room temperature for 0.5 h, followed by the addition of water (160 mL) dropwise over 1 h. The solution is seeded with imidazole 4 and followed by the addition of water (160 mL) dropwise over 1 h. The product precipitated within 0.5 h. The slurry is aged at room temperature for 2 h, cooled to 10° C., aged for 0.5 h and the solid is filtered. The cake is washed with 320 mL of water, suction dried under nitrogen at room temperature for 2 h and oven dried under house vacuum (−24 psi) at <60° C. for 12 h to afford 54.3 g of titled midazole as a white solid (HPLC assay: 98.8 A %, 97.2 W %, overall yield: 92.4%, 0.5 W % of the regioisomer).

EXAMPLE 7

2-n-Butyl-4-chloro-1-[(2'-(2-triphenylmethyl-2H-tetrazol-5-yl)-1,1'-biphenyl-4-yl)methyl]-1H-imidazole-5-methanol Step A: Catalyst Preparation Triphenylphosphine (262 mg, 1.0 mmol) is dissolved in THF (20 mL) and the solution is degassed by vacuum/nitrogen purges (3×). Palladium acetate (56 mg, 0.25 mmol) is added and the solution is degassed again (3×). The resulting solution is warmed to 60° C. for 30 min. and then cooled to 25° C.
Step B: Coupling
Note: All solvents must be degassed.

2-(2'-triphenylmethyl-2'H-tetrazol-5'-yl)phenylboronic acid (15.4 g, 26.7 mmol, 75 wt % pure) is suspended in diethoxymethane (DEM) (80 mL, KF≦500 mg/ml). Water (0.55 mL, 31 mmol) is added and the slurry is aged at ambient temperature for 30 min. After the age, another charge of water (0.55 ml, 31 mmol) is added to the boronic acid suspension under agitation. The slurry is then treated with powdered potassium carbonate (8.6 g, 62 mmol) and alkylated imidazole, the titled product of Example 22 (8.97 g, 25 mmol). The mixture is aged at 20–25° C. for 30 min then degassed well (3×). (Note: in the pilot plant, degassing takes much longer and can be started immediately after the imidazole and carbonate are added). The catalyst solution is then charged and the mixture is heated to reflux (76–79° C.). The reaction is complete in 2–6 hours. When the imidazole has been consumed, water (30 mL) and THF (25 ml) are added and the mixture is stirred at 55–60° C. The water layer is separated and the organic layer is washed with water (30 mL). The organic layer is concentrated in vacuo to a volume of 50 ml to remove most of the THF. More DEM (50 ml) is added and removed by distillation to further reduce THF to ≦5vol %. The residual organic solution is diluted with warm (60° C.) DEM (to a final volume of 75 ml) and water (0.5 ml, 28 mmol). The mixture is then cooled slowly to −12° C. over 2 hours. After aging at −12° C. for 1 hour, the product is collected by filtration. The cake is washed with cold DEM (25 mL). Vacuum drying at 40° C. gave 15.5 g (93%) of the titled product (non-solvated). [Pd=600 to 1000 ppm.]

EXAMPLE 8

2-n-Butyl-4-chloro-1-[(2'-(2-triphenylmethyl-2H-tetrazol-5-yl)-1,1'-biphenyl-4-yl)methyl]-1H-imidazole-5-methanol Step A: Catalyst Preparation
Triphenylphosphine (262 mg, 1.0 mmol) is dissolved in THF (20 mL) and the solution is degassed by vacuum/nitrogen purges (3×). Palladium acetate (56 mg, 0.25 mmol) is added and the solution is degassed again (3=). The resulting solution is warmed to 60° C. for 30 min. and then cooled to 25° C.
Step B: Coupling
Note: All solvents must be degassed.

2-(2'-Triphenylmethyl-2'H-tetrazol-5'-yl)phenylboronic acid (15.4 g, 26.7 mmol, 75 wt % pure) is suspended in diethoxymethane (DEM) (80 mL, KF≦500 mg/ml). Water (0.55 mL, 31 mmol) is added and the slurry is aged at ambient temperature for 30 min. After the age, another charge of water (0.55 ml, 31 mmol) is added to the boronic acid suspension under agitation. The slurry is then treated with powdered potassium carbonate (8.6 g, 62 mmol) and the titled product of Example 22, the alkylated imidazole (8.97 g, 25 mmol). The mixture is aged at 20–25° C. for 30 min then degassed well (3×). (Note: in the pilot plant, degassing takes much longer and can be started immediately after the imidazole and carbonate are added). The catalyst solution is then charged and the mixture is heated to reflux (76–79° C.). The reaction is complete in 2–6 hours. When the imidazole has been consumed, water (30 mL) and THF (25 ml) are lo added and the mixture is stirred at 55–60° C. The water layer is separated and the organic layer is washed with water (30 mL). Tributylphosphine (0.62 ml, 10 mol %) is added and the organic layer is concentrated in vacuo to a volume of 50 ml to remove most of the THF. More DEM (50 ml) is added and removed by distillation to further reduce THF to ≦5 vol %. The residual organic solution is diluted with warm (60° C.) DEM (to a final volume of 75 ml) and water (0.5 ml, 28 mmol). The mixture is then cooled slowly to −12° C. over 2 hours. After aging at −12° C. for 1 hour, the product is collected by filtration. The cake is washed with cold DEM (25 mL). Vacuum drying at 40° C. gave 15.5 g (93%) of the titled product (non-solvated). [Pd≦10 ppm].

EXAMPLE 9

2-n-Butyl-4-chloro-1-[(2'-(2-triphenylmethyl-2H-tetrazol-5-yl)-1,1'-biphenyl-4-yl)methyl]-1H-imidazole-5-methanol as the methyl isobutyl ketone solvate A suspension of the titled product of Example 7 (5g) in methyl isobutyl ketone (MIBK) (40 ml) is degassed (3×) and tributylphosphine (0.12 g, 8 mol %) is added. The mixture is heated to 85° C. at which time a homogeneous solution was obtained. Degassed water (0.135 g, 100 mol %) is then added and the solution is cooled to −10° C. over 2 hours. The heterogeneous solution is aged at −10° C. for 2 hours, the crystallized product is collected by filtration and washed with cold MIBK (−10° C., 15 ml). The recovery was 5.40 g of the titled product (93.9%, as the MIBK solvate).

EXAMPLE 10

2-n-butyl-4-chloro-1-[(2'-(tetrazol-5-yl)-1,1'-biphenyl-4-yl)-methyl]-1H-imidazole-5-methanol potassium salt
Step A: Deprotection
Dissolve 2.50 g of the titled product of Example 8, the methyl isobutyl ketone solvate, by adding 10 mL of 0.75 M $H_2SO_4$ in 50:50 MeCN:water. Age 2 hours 25 min, 23–25° C. Add 15 mL of water in 2 min (can be added in 30 min to an hour in larger scales), and age 1.75 hours, 23–25° C. Filter and wash with 5 mL of 20:80 MeCN:water. There was almost no starting material left in the trityl alcohol filter cake (<0.05 area %).
Step B: Free Acid Formation
Dilute the above filtrate with 13 mL of MeCN. The pH of the solution is 1.50. The temperature of the solution following neutralization and crystallization was 22–24° C. After adding 1.5 mL of 3 N NaOH (pH 1.75–1.65), the reaction is seeded with 20 mg of the free acid. Age 15 min. Slowly add the next 1 mL of 3 M NaOH to allow for good crystal growth (on this scale, the addition time was 5–10 min). Age 30 min. Add the remaining 3 M NaOH (pH 3.60–3.50). Age 1 hour. The white slurry is filtered and washed with 5 mL of 20:80 MeCN:water then 10 mL of water. A thorough water wash of the free acid filter cake is necessary to remove all the salts. The wash can be checked for $SO_4^{-2}$. The filter cake is dried in a vacuum oven at 35° C. for 18 hours with nitrogen purge. The yield of the free acid was 1.28 g (92.5%) and there was 54 mg (4%) of the free acid in the mother liquors.
Step C: Salt Formation
To 4.0 g (9.46 mmoles) of the free acid is added 10.9 ml of 0.842N KOH solution all in one portion. The slurry is aged at room temperature for 30 minutes, during which time most of the solid dissolves. The cloudy solution is filtered and the solids collected on a sintered glass funnel. The pH of the filtrate is measured at 9.05. The aqueous solution is added slowly to a refluxing azeotropic mixture of cyclohexane/isopropanol (69° C.) whereupon the ternary azeotrope cyclohexane/isopropanol/water (64° C.) begins to distill. When the solution is dry the temperature of the overhead rises to 69° and the potassium salt crystallizes. When the water content of the pot is <0.05% the distillation is halted and the white slurry is cooled to room temperature. The white crystalline solid is collected on a sintered glass funnel and washed with 10–15 ml of cyclohexane/isopropanol 67/33 and dried in a vacuum oven. (wt 3.8 g yield 95%).

Utility

The hormone angiotensin II (AII) produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Glossmann, et al., *J. Biol. Chem.*, 249, 825 (1974)], but with some modifications. The reaction mixture contained rat adrenal cortical microsomes (source of AII receptor) in Tris buffer and 2 nM of $^3$H-AII with or without potential AII antagonist. This mixture was incubated for 1 hour at room temperature and the reaction was subsequently terminated by rapid filtraton and rinsing through glass micro-fibre filter. Receptor-bound $^3$H-AII trapped in filter was quantitiated by scintillation counting. The inhibitory concentration ($IC_{50}$) of potential AII antagonist which gives 50% displacement of the total specifically bound $^3$H-AII is presented as a measure of the affinity of such compound for the AII receptor (See Tables 1 and 2).

The potential antihypertensive effects of the compounds of this invention may be demonstrated by administering the compounds to awake rats made hypertensive by ligation of the left renal artery [Cangiano, et al., *J. Pharmacol. Exp. Ther.*, 208, 310 (1979)]. This procedure increases blood pressure by increasing renin production with consequent elevation of AII levels. Compounds are administered orally at 100 mg/kg and/or intravenously via a cannula in the jugular vein at 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds (See Table 1).

TABLE 1

| Ex. No. | Angiotensin II Receptor Binding $IC_{50}$ ($\mu$molar) | Antihypertensive Effects in Renal Hypertensive Rats | |
|---|---|---|---|
| | | Intravenous Activity[1] | Oral Activity[2] |
| Losartan | 0.039 | + | + |

[1]Significant decrease in blood pressure at 10 mg/kg or less
[2]Significant decrease in blood pressure at 100 mg/kg or less Compounds listed in Table 2 were tested in the same manner as described for Table 1, except that in the test for antihypertensive effects in renal hypertensive rats, the compounds were administered orally at 30 mg/kg and intravenously at 3 mg/kg.

TABLE 2

| Ex. No. | Angiotensin II Receptor Binding $IC_{50}$ ($\mu$molar) | Antihypertensive Effects in Renal Hypertensive Rats | |
|---|---|---|---|
| | | Intravenous Activity[1] | Oral Activity[2] |
| EXP-3174 | 0.011 | + | + |

[1]Significant decrease in blood pressure at 3.0 mg/kg or less
[2]Significant decrease in blood pressure at 30 mg/kg or less The hypotensive effects of 2-butyl-4-chloro-1-[2'-(1H-tetrazol-5-yl)biphenyl-4-yl)methyl]-5-hydroxymethylimidazole sodium salt were compared before and after furosemide administration to conscious dogs. Cumulative intravenous injections of imidazole at 0.3 to 3 mg/kg did not lower blood pressure in normotensive conscious Dogs (n=4, FIG. 1) but they were effective in inhibiting the pressor response to AII (0.1 μg/kg iv) determined at 10 min post dose (FIG. 2). Plasma renin activity (PRA) in these animals was 1.5±0.5 ng AI/ml/hr. Four days later, furosemide was given to three of these dogs at 10 mg/kg im at 18 and 2 hours before the experiment and increased PRA to 19.9±7.2 ng AI/ml/hr. 1 midazole was then given cumulatively iv at the same doses and caused a significant decrease in blood pressure in a dose-dependent manner (FIG. 1). It also inhibited the pressor response to AII at the two higher doses (FIG. 2). A similar hypotensive enhancement by furosemide was also observed with captopril at 0.3 mg/kg iv (FIG. 2). These results indicate that diuretics enhance the hypotensive efficacy of imidazole AII blockers. Thus a combined therapy of these two classes of drugs will be likely to increase the response rate to therapy among hypertensive patients.

Protocol Utilized for the Determination of the
Effects of Losartan, an Angiotensin II Antagonist,
on Insulin Sensitivity and Sympathetic Nervous
System Activity The effects of 2-butyl-4-chloro-1-[2'-(1H-tetrazol-5-yl) biphenyl-4-yl)methyl]-5-hydroxymethylimidazole potassium salt (Losartan) on insulin sensitivity and sympathetic nervous system activity were studied in patients with severe hypertension, which is defined as previously untreated diastolic blood pressure ≧115 mm Hg. At the time of the study only a three day wash-out period was allowed due to the severity of their hypertension.

Losartan was administered in a 50 mg oral dose once a day for the first two weeks, and increased to a 100 mg oral dose once a day, if the patient's diastolic blood pressure ≧95 mmHg at any of the clinic visits which occurred every second week. A euglycemic glucose clamp procedure was performed three days after the initial screening, and after withdrawl from previous antihypertensive medications. This procedure was repeated at the end of Losartan montherapy, which averaged about 6 weeks, ranging from 3 to 12 weeks.

The euglycemic hyperinsulinemic glucose "clamp" was performed using a modification of the method described by DeFronzo, et al. *Am. J. Physiol.* 1979:237: E214–23, as previously detailed by Moan, et al., *Metabolism*, in press. Insulin was infused at a fixed rate of 1 mU/kg/min. This technique for measuring the glucose disposal rate has a day-to-day coefficient of less than 5% percent. The average plasma insulin level was found to be 85±11 mU/l during the first clamp and 80±7 mU/l during the second clamp. The steady state levels of insulin varied from one person to another, and as a result the insulin sensitivity index was also calculated. This index is a ratio of the glucose disposal rate to the mean level of insulin during the last 20 minutes of the glucose clamp multiplied by 100, and is given arbitrary units. Blood for baseline adrenaline and noradrenaline were sampled in duplicate and the results averaged.

Fasting glucose was determined enzymatically, using a glucose dehydrogenase method and a Cobas Bio analyzer (Roche, Basel Switzerland). A Reflolux II (Mannheim Boehringer GmbH, Mannheim, Germany) was utilized to measure glucose concentration during the glucose clamp procedure (within run coefficient of variation <3% in our laboratory). Fructosamine was determined by calorimetric method. Insulin was measured by radioimmunoassay technique, using a specific antibody from Linco Research Inc. (St. Louis, Mo., USA). The lower limit of detection is 5 mU/l cross reactivity with proinsulin less than 1% and intra-assay coefficient of variation below 9% at all levels. Plasma catecholamines from specialized venous blood were measured by the radioenzymatic technique of Peuler Johnson as detailed in Kjelsen et al., Scan. J. Clin. Invest. 1993:42:217–23. Blood pressure and heart rate were measured oscillometrically with an Omega 1000™ Adult/Pediatric Blood Pressure Recorder (INVIVO Research Laboratories Inc., Tulsa Okla., USA).

Statistical Analysis

Differences were analyzed by the Wilcoxon signed rank test using the satistical package SPSS PC+ Version 4.0 (SPSS PC+ Inc., Chicago, Ill., USA). The level of significance was set at $p \leq 0.05$ one tailed for blood pressure and two-tailed for all other parameters. Data are presented as means±SD.

Results

The glucose disposal rate increased in all patients from 6.2±2.6 to 7.9±2.6 mg/kg×min.(27%, $p<0.05$). The insulin sensitivity index increased from 7.7±4.5 to 10.1±4.1 arbitrary units (30%, $p<0.05$). This was accompanied by non-significant decreases in fasting glucose (5.0±0.3 to 4.8±0.1 mmol/l) and fructosamine (227±18 to 217±11 $\mu$mol/l), while the fasting serum insulin was unchanged (12±3 vs. 12±2 mU/l).

There was a significant decrease in baseline plasma noradrenaline from 1.87±0.53 to 1.11±0.13 nmol/l (40%, $p<0.05$), while plasma adrenaline remained unchanged (0.23±0.10 vs. 0.22±0.11 nmol/l, n.s.). Baseline mean blood pressure decreased from 132±10 to 119±13 mmHg ($p<0.05$) during the treatment period. Baseline heart rate remained unchanged (65±9 vs. 68±12 beats/min, n.s.).

In addition to a fall in blood pressure, administration of Losartan for an average of six weeks was found to increase the glucose disposal rate. Losartan specifically blocks angiotensin II induced vasoconstriction therefore causing vasodilation, and is believed to cause an increase in glucose delivery to skeletal muscle. This results seen with Losartan corresponds well with the effects known to occur with other vasodilatory antihypertensive drugs, ACE inhibitors, $Ca^{+2}$ channel blockers and ($\alpha$-blockers, on insulin mediated glucose disposal, and supports the hemodunamic basis of insulin resistance in hypertension as suggested by Julius et al. Blood Pressure 1992:1:9–19.

The decrease in plasma noradrenaline by Losartan suggests a sympatholytic effect which together with vasodilation is an explanation for the improvement in insulin sensitivity.

DOSAGE FORMS

The compounds of this invention can be administered for the treatment of hypertension according to the invention by any means that effects contact of the active ingredient compound with the site of action in the body of a warm-blooded animal. For example, administration, can be parenteral, i.e., subcutaneous, intravenous, intramuscular or intra peritoneal. Alternatively, or concurrently in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts both for treatment of hypertension and for treatment of congestive heart failure, i.e., for lowering blood pressure and for correcting the hemodynamic burden on the heart to relieve the congestion.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gyclols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In additiion, parenteral solutions can contain preservatives, such as benzalkonium chloride, methyl- or propylparaben, and chlorobutanol.

Suitable pharmaceutical carriers are described in Remington's Pharmaceutical Sciences, A. Osol, a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive olil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.9 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When drugs are administered in physical combination, the dosage form and administration route should be selected for compatibility with both drugs. Suitable dosages, dosage forms and admnistration routes are illustrated in Table 3.

TABLE 3

Examples of diuretics that can be combined with AII blockers of this invention:

| Drug | Dose | Formulation | Route |
|---|---|---|---|
| Benzothiadizides (e.g. hydrochlorothiazide) | 5–100 mg (daily) | Tablet | Oral |
| Loop diuretics (e.g. furosemide) | 50–80 mg (daily) | Tablet | Oral |

When used with diuretics, the initial dose of AII blocker can be less, e.g., 1–100 milligrams per day and for the more active compounds 1–10 milligrams per day.

What is claimed is:

1. A method of improving insulin sensitivity alone or in conjunction with the treatment of hypertension using an angiotensin II antagonist.

2. A method of improving insulin sensitivity alone or in conjunction with the treatment of hypertension using an angiotensin II antagonist of formula I:

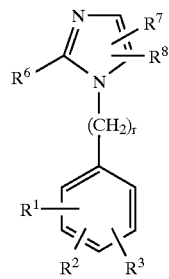

wherein:

$R^1$ is:
   4-$CO_2H$; 4-$CO_2R^9$;

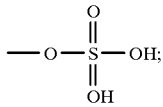

—$SO_3H$; —$C(CF_3)_2OH$;

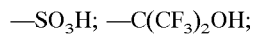

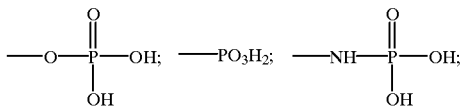

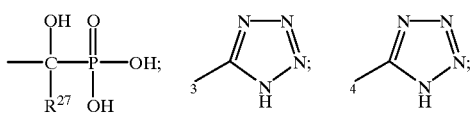

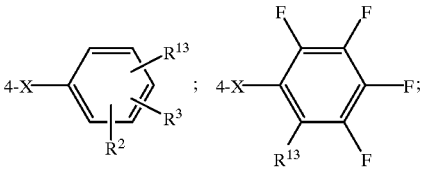

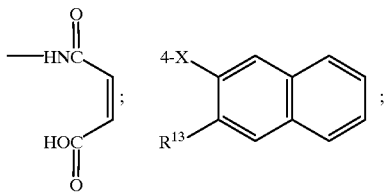

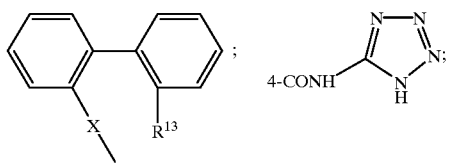

-continued

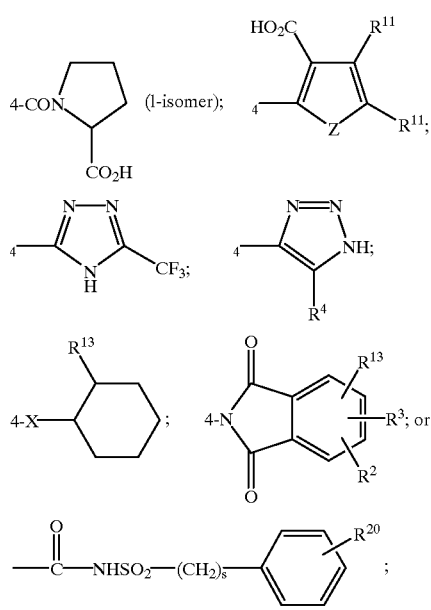

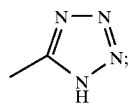

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $HNSO_2CH_3$; $NHSO_2CF_3$; $CONHOR^{12}$; $SO_2NH_2$;

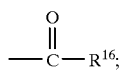

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl 5 to 10 carbon atoms; $(CH_2)_sZ(CH_2)_mR^5$ optionally substituted with F or $CO_2R^{14}$; benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1–6, $C_6F_5$; CN;

$$\overset{O}{\underset{\|}{-C}}-R^{16};$$

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; —$(CH_2)_m$-imidazol-1-yl; —$(CH_2)_m$-1,2,3-triazolyl optionally substituted with one or two group selected from $CO_2CH_3$ or alkyl of 1 to 4 carbon atoms; —$(CH_2)_s$ tetrazolyl;

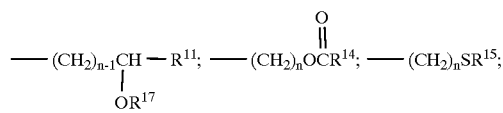

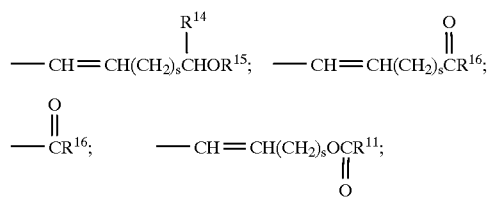

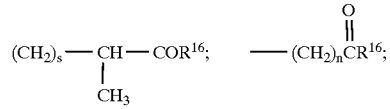

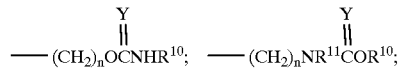

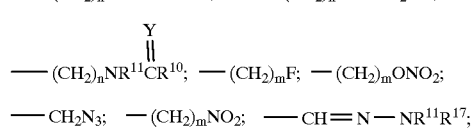

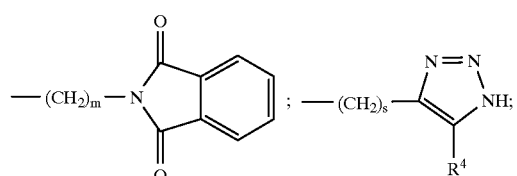

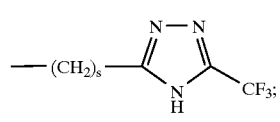

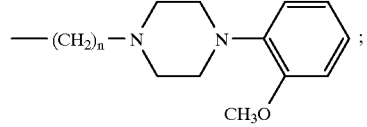

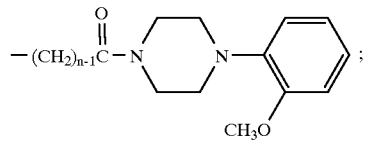

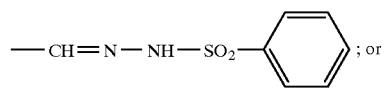

-continued

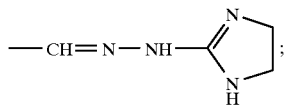

$R^9$ is:

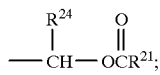

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is $-CO_2H$; $-CO_2R^9$; $-CH_2CO_2H$, $-CH_2CO_2R^9$;

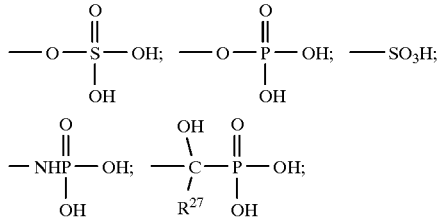

$-PO_3H_2$; $-C(CF_3)_2OH$; $-NHSO_2CH_3$; $-NHSO_2CF_3$; $-NHCOCF_3$; $-CONHOR^{12}$; $-SO_2NH_2$;

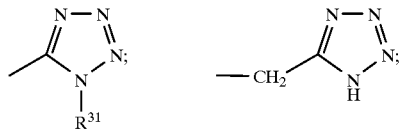

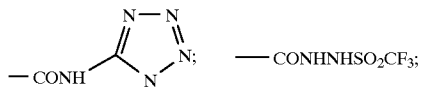

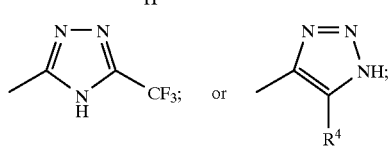

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

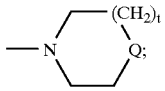

Q is $NR^{20}$, O or $CH_2$;

$R^{20}$ is H, alkyl of 1–4 carbon atoms, or phenyl;

$R^{21}$ is alkyl of 1 to 6 carbon atoms, $-NR^{22}R^{23}$, or

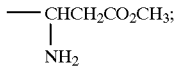

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $-C_6H_5$;

$R^{25}$ is $NR^{27}R^{28}$, $OR^{28}$, $NHCONH_2$, $NHCSNH_2$,

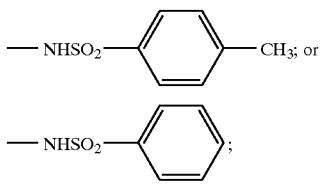

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $-(CH_2)_q-$;

$R^{31}$ is H, alkyl or 1 to 4 carbon atoms, $-CH_2CH=CH_2$ or $-CH_2C_6H_4R^{32}$;

X is a carbon-carbon single bond, $-CO-$, $-CH_2-$, $-O-$, $-S-$, $-NH-$,

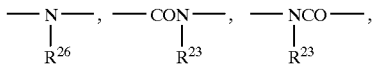

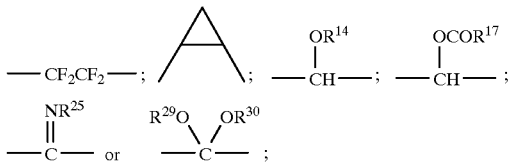

Y is O or S;

Z is O, $NR^{11}$, or S;

m is 1 to 5;

n is 1 to 10;

p is 0 to 3;

q is 2 to 3;

r is 0 to 2;

s is 0 to 5;

t is 0 or 1;

and pharmaceutically acceptable salts of these compounds; provided that:

(1) the $R^1$ group is not in the ortho position;

(2) when $R^1$ is

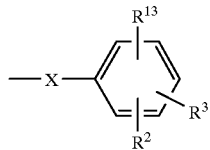

X is a single bond, and $R^{13}$ is $CO_2H$, or

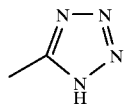

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

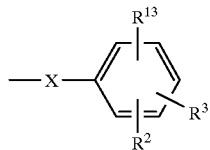

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

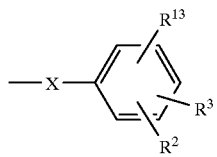

X is —$OCH_2$—, and $R^{13}$ is 2-$CO_2H$, and $R^7$ is H then $R^6$ is not $C_2H_5S$;

(7) when $R^1$ is

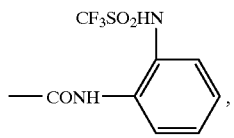

and $R^6$ is n-hexyl then $R^7$ and $R^8$ are not both hydrogen;

(8) when $R^1$ is

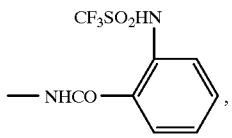

$R^6$ is not methoxybenzyl;

(9) the $R^6$ group is not

or $CH_2OH$;

(10) when r=0, $R^1$ is

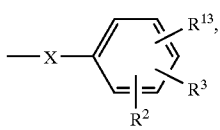

X is

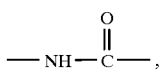

$R^{13}$ is 2-$NHSO_2CF_3$, and $R^6$ is n-propyl, then $R^7$ and $R^8$ are not —$CO_2CH_3$;

(11) when r=0, $R^1$ is

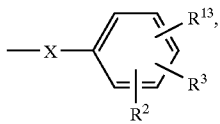

X is

$R^{13}$ is 2-COOH, and $R^6$ is n-propyl, then $R^7$ and $R^8$ are not —$CO_2CH_3$;

(12) when r=1, $R^1$ is

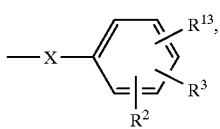

X is a single bond, $R^7$ is Cl, and $R^8$ is —CHO, then $R^{13}$ is not 3-(tetrazol-5-yl);

(13) when r=1, $R^1$ is

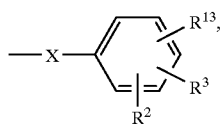

X is a single bond, $R^7$ is Cl, and $R^8$ is —CHO, then $R^{13}$ is not 4-(tetrazol-5-yl).

3. The method according to claim 2, wherein the compounds have the formula:

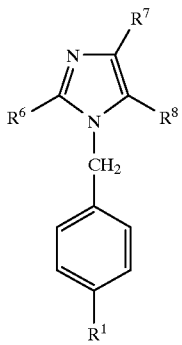

wherein:

$R^1$ is —$CO_2H$; —$NHSO_2CF_3$;

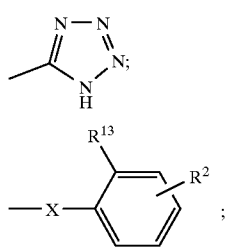

or

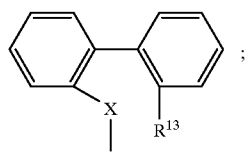

$R^6$ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, and nitro;

$R^8$ is phenylalkenyl wherein the aliphatic portion is 2 to 4 carbon atoms, —$(CH_2)_m$-imidazol-1yl, —$(CH_2)_m$1,2,3-triazolyl optionally substituted with one or two groups selected from $CO_2CH_3$ or alkyl of 1 to 4 carbon atoms, $(CH_2)_m$-tetrazolyl, —$(CH_2)_nOR^{11}$;

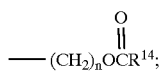

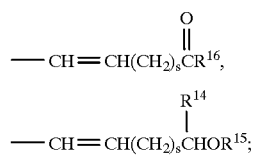

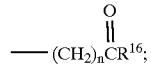

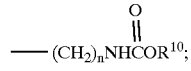

—$(CH_2)_nNHCOR^{10}$;

—$(CH_2)_nNHSO_2R^{10}$;

—$(CH_2)_mF$;

$R^{13}$ is —$CO_2H$, —$CO_2R^9$, $NHSO_2CF_3$; $SO_3H$;

or

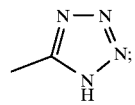

$R^{16}$ is H, alkyl of 1 to 5 carbon atoms, $OR^{17}$, or $NR^{18}R^{19}$;

X is carbon-carbon single bond, —CO—,

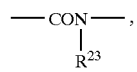

—$CH_2CH_2$—,

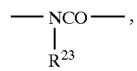

—$OCH_2$—, —$CH_2O$—, —$SCH_2$—, —$CH_2S$—, —$NHCH_2$—, —$CH_2NH$— or —CH=CH—; and pharmaceutically acceptable salts of these compounds.

4. The method according to claim 2, wherein:

$R^2$ is H, alkyl of 1 to 4 carbon atoms, halogen, or alkoxy of 1 to 4 carbon atoms;

$R^6$ is alkyl, alkenyl or alkynyl of 3 to 7 carbon atoms;

$R^7$ is H, Cl, Br, $C_vF_{2v+1}$, where v=1–3, or

$R^8$ is —$(CH_2)_mOR^{11}$;

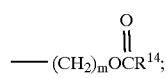

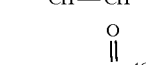

-continued

—(CH$_2$)$_m$NHSO$_2$R$^{10}$;

or —COR$^{16}$;

R$^{10}$ is CF$_3$, alkyl of 1 to 6 carbon atoms or phenyl;

R$^{11}$ is H, or alkyl of 1 to 4 carbon atoms;

R$^{13}$ is CO$_2$H; CO$_2$CH$_2$OCOC(CH$_3$)$_3$; NHSO$_2$CF$_3$; and

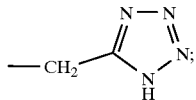

R$^{14}$ is H, or alkyl of 1 to 4 carbon atoms;

R$^{15}$ is H, alkyl of 1 to 4 carbon atoms, or acyl of 1 to 4 carbon atoms;

R$^{16}$ is H, alkyl of 1 to 5 carbon atoms; OR$^{17}$; or

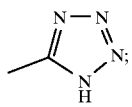

m is 1 to 5;

X is single bond, —O—; —CO—; —NHCO—; or —OCH$_2$—; or a pharmaceutically acceptable salts.

5. The method according to claim 2, wherein the compound of formula I is selected from the group consisting of:

2-Butyl-4-chloro-1-[(2'-(1H-tetrazol-5-yl)biphenyl-4-yl)methyl]-5-(hydroxymethyl)imidazole;

2-Butyl-4-chloro-1-[(2'-carboxybiphenyl-4-yl)methyl]-5-(hydroxymethyl)imidazole;

2-Butyl-4-chloro-1-[(2'-carboxybiphenyl-4-yl)methyl]-5-[(methoxycarbonyl)aminomethyl]imidazole;

2-Butyl-4-chloro-1-[(2'-carboxybiphenyl-4-yl)methyl]-5-[(propoxycarbonyl)aminomethyl]imidazole;

2-Butyl-4-chloro-1-[(2'-carboxybiphenyl-4-yl)methyl]imidazole-5-carboxaldehyde;

2-Butyl-1-[(2'-carboxybiphenyl-4-yl)methyl]-imidazole-5-carboxaldehyde;

2-(1E-Butenyl)-4-chloro-1-[(2'-carboxybiphenyl-4-yl)methyl]-5-(hydroxymethyl)imidazole;

2-(1E-Butenyl)-4-chloro-1-[(2'-carboxybiphenyl-4-yl)methyl]-imidazole-5-carboxaldehyde;

2-Propyl-4-chloro-1-[(2'-(1H-tetrazol-5-yl)biphenyl-4-yl)methyl]-5-(hydroxymethyl)imidazole;

2-Propyl-4-chloro-1[(2'-(1H-tetrazol-5-yl)biphenyl-4-yl)methyl]-imidazole-5-carboxaldehyde;

2-Butyl-4-chloro-1-[2'-(1H-tetrazol-5-yl)biphenyl-4-yl)methyl]-imidzole-5-carboxaldehyde;

2-(1E-Butenyl)-4-chloro-1[(2'-(1H-tetrazol-5-yl)biphenyl-4-yl)methyl]-5-hydroxymethyl)imidazole;

2(1E-Butenyl)-4-chloro-1-[(2'-(1H-tetrazol-5-yl)biphenyl-4-yl)methyl]imidazole-5-carboxaldehyde;

2-Butyl-4-chloro-1-[(2'-(1H-tetrazol-5-yl)-biphenyl-4-yl)methyl]-imidazole-5-carboxylic acid;

2-Propyl-4-chloro-1-[(2-'(1H-tetrazol-5-yl)-biphenyl-4-yl)methyl]-imidazole-5-carboxylic acid;

2-Propyl-4-trifluoromethyl-1-[(2'-(1H-tetrazol-5-yl)biphenyl-4-yl)methyl]imidazole-5-carboxylic acid;

2-Propyl-4-trifluoromethyl-1-[(2'-(1H-tetrazol-5-yl)biphenyl-4-yl)methyl]-5-(hydroxylmethyl)imidazole;

2-Butyl-4-trifluoromethyl-1-[(2'-(1H-tetrazol-5-yl)biphenyl-4-yl)methyl]imidazole-5-carboxylic acid;

2-Propyl-4-trifluoromethyl-1-[(2'-(carboxybiphenyl-4-yl)methyl]-imidazole-5-carboxaldehyde;

2-Propyl-4-pentafluoroethyl-1-[(2'-(1H-tetrazol-5-yl)biphenyl-4-yl)methyl]-5-(hydroxymethyl)imidazole;

2-Propyl-1-[(2-(1H-tetrazol-5-yl)biphenyl-4-yl)methyl]imidazole-4,5,-dicarboxylic acid;

2-Propyl-4-pentafluoroethyl-1-[(2'-(1H-tetrazol-5-yl)biphenyl-4-yl)methyl]imidazole-5-carboxylic acid;

2-Propyl-4-pentafluoroethyl-[(2'-(1H-tetrazol-5-yl)biphenyl-4-yl)methyl]imidazole-5-carboxaldehyde, or a pharmaceutically acceptable salt thereof.

6. The method according to claim 2, wherein the compound of formula I is selected from the group consisting of:

2-Butyl-4-chloro-1-[(2'-tetrazol-5-yl)biphenyl-4-yl]methyl]-5-(hydroxymethyl)imidazole; and 2-Butyl-4-chloro-1-[(2'-tetrazol-5-yl)biphenyl-4-yl]methylimidazole-5-carboxylic acid or a pharmaceutically acceptable salt thereof.

7. The method according to claim 2, wherein the compound is 2-Butyl-4-chloro-1-[(2'-tetrazol-5-yl)biphenyl-4-yl]methyl]-5-(hydroxymethyl)imidazole potassium salt.

* * * * *

UNITED STATES PATENT AND TRADEMARK OFFICE
CERTIFICATE OF CORRECTION

PATENT NO. : 5,962,500

DATED: October 5, 1999

INVENTOR(S): Ivar K. Eide, Andreas Moan and Sverre E. Kjeldsen

It is certified that errors by the USPTO appear in the above-identified patent and that said Letters Patent is hereby corrected as shown below:

In column 30, claim 2, between lines 37 and 40 please replace the structure with:

-- 4-NHSO$_2$CH$_3$; 4-NHSO$_2$CF$_3$; -CONHOR$^{12}$; -SO$_2$NH$_2$; -- .

In column 32, claim 2, between lines 32 and 35 please replace the structure with:

$$-\text{(CH}_2\text{)}_n\text{NR}^{11}\overset{\overset{\text{O}}{\|}}{\text{C}}\text{NHR}^{10}; \quad -\text{(CH}_2\text{)}_n\text{NR}^{11}\text{SO}_2\text{R}^{10};$$

Signed and Sealed this

Twenty-seventh Day of June, 2000

*Attest:*

Q. TODD DICKINSON

*Attesting Officer*       *Director of Patents and Trademarks*